US010471027B2

(12) United States Patent
Kubota et al.

(10) Patent No.: US 10,471,027 B2
(45) Date of Patent: *Nov. 12, 2019

(54) PHARMACOLOGY OF VISUAL CYCLE MODULATORS

(75) Inventors: Ryo Kubota, Seattle, WA (US); Nancy Boman, Bothell, WA (US); Claes Bavik, Bothell, WA (US); Ian L. Scott, Monroe, WA (US)

(73) Assignee: ACUCELA, INC., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/830,155

(22) Filed: Jul. 2, 2010

(65) Prior Publication Data
US 2011/0003895 A1 Jan. 6, 2011

Related U.S. Application Data

(60) Provisional application No. 61/222,875, filed on Jul. 2, 2009, provisional application No. 61/266,922, filed on Dec. 4, 2009.

(51) Int. Cl.
*A61K 31/135* (2006.01)
*A61K 31/137* (2006.01)
*A61K 31/166* (2006.01)
*A61K 9/00* (2006.01)
*A61K 9/50* (2006.01)
*A61K 31/19* (2006.01)
*A61K 31/195* (2006.01)

(52) U.S. Cl.
CPC .......... *A61K 31/166* (2013.01); *A61K 9/0048* (2013.01); *A61K 9/5078* (2013.01); *A61K 31/135* (2013.01); *A61K 31/137* (2013.01); *A61K 31/19* (2013.01); *A61K 31/195* (2013.01); *Y10S 514/912* (2013.01)

(58) Field of Classification Search
USPC ......................................................... 514/646
See application file for complete search history.

(56) References Cited

U.S. PATENT DOCUMENTS

| | | | |
|---|---|---|---|
| 3,105,854 A | 10/1963 | Druey et al. | |
| 3,644,353 A | 2/1972 | Lunts et al. | |
| 3,987,158 A | 10/1976 | Hodson | |
| 4,214,001 A | 7/1980 | Engelhardt | |
| 5,049,587 A | 9/1991 | Okamoto | |
| 5,135,955 A | 8/1992 | Campbell et al. | |
| 5,314,879 A | 5/1994 | Camaggi et al. | |
| 5,475,034 A | 12/1995 | Yanni et al. | |
| 5,541,228 A | 7/1996 | Takaki et al. | |
| 5,541,343 A | 7/1996 | Himmelsbach et al. | |
| 5,661,185 A | 8/1997 | Takaki et al. | |
| 6,051,605 A | 4/2000 | Capiris et al. | |
| 6,162,943 A | 12/2000 | Lui et al. | |
| 6,271,385 B1 | 8/2001 | Ito et al. | |
| 6,713,458 B1 | 3/2004 | Yerxa et al. | |
| 7,220,780 B2 | 5/2007 | Slusher et al. | |
| 7,982,071 B2 | 7/2011 | Scott et al. | |
| 8,829,244 B2 | 9/2014 | Scott et al. | |
| 8,993,807 B2 * | 3/2015 | Scott ..................... | C07C 217/20 564/323 |
| 2002/0058685 A1 | 5/2002 | Hamilton | |
| 2003/0032078 A1 | 2/2003 | Travis | |
| 2003/0186961 A1 | 10/2003 | Hamilton et al. | |
| 2003/0186981 A1 | 10/2003 | Duplantier et al. | |
| 2005/0101783 A1 | 5/2005 | Ito et al. | |
| 2006/0069078 A1 | 3/2006 | Rando | |
| 2006/0252107 A1 | 11/2006 | Kubota et al. | |
| 2006/0281821 A1 | 12/2006 | Palczewski et al. | |
| 2009/0326074 A1 | 12/2009 | Scott et al. | |
| 2011/0003895 A1 | 1/2011 | Kubota et al. | |
| 2012/0122938 A1 | 5/2012 | Scott et al. | |
| 2012/0129894 A1 | 5/2012 | Scott et al. | |
| 2012/0214852 A1 | 8/2012 | Scott et al. | |
| 2017/0049722 A1 | 2/2017 | Scott et al. | |
| 2018/0177746 A1 | 6/2018 | Scott et al. | |

FOREIGN PATENT DOCUMENTS

| | | |
|---|---|---|
| CH | 396941 | 8/1965 |
| EP | 0133259 A2 | 2/1985 |
| EP | 0525360 | 2/1993 |
| EP | 0706994 A1 | 4/1996 |
| EP | 1661881 A2 | 5/2006 |
| GB | 884663 | 11/1959 |
| JP | S50112386 A | 9/1975 |
| JP | H04264068 A | 9/1992 |

(Continued)

OTHER PUBLICATIONS

National Eye Institute, Facts About Stargardt Disease, Apr. 2015, National Institute of Health, printed from https://nei.nih.gov/health/stargardt/star_facts on Nov. 22, 2016, 6 pages.*
Golczak et al., "Positively charged retinoids are potent and selective inhibitors of the trans-cis isomerization in the retinoid (visual) cycle," PNAS 102(23): 8162-8167 (2005).
PCT/US10/40983 Search Report and Written Opinion dated Mar. 31, 2011.
Epstein, E., "Alkoxyphenyl N-Substituted Aminopropanols," *J. Am. Chem. Soc.* 81(23):6207-6209 (1959).
Ettmayer et al., "Lessons Learned from Marketed and Investigational Prodrugs," *J Med Chem* 47(10):2393-2404 (2004).
GB0818175.2 Search Report dated Jan. 12, 2009.
Kano et al., A Synthesis of Dibenz[b,f]azecines from 1-halogenobenzyl-1H-2-benzazepines, *Chem Pharm Bull* 25(9):2401-2409 (1977).
Maeda et al., "Evaluation of the role of the retinol G protein-coupled receptor (RGR) in the vertebrate retina in vivo," *J. Neurochem.* 85(4):944-956 (2003).

(Continued)

*Primary Examiner* — Gigi G Huang
(74) *Attorney, Agent, or Firm* — Wilson Sonsini Goodrich & Rosati

(57) ABSTRACT

Described herein are methods for the treatment of an ophthalmic disease or disorder comprising the administration of non-retinoid visual cycle modulators. Ophthalmic diseases and disorders which can be treated according to the methods provided herein include age-related macular degeneration (AMD), Stargardt's disease, glaucoma, and other disorders that adversely affect the retina.

19 Claims, 13 Drawing Sheets

(56) References Cited

FOREIGN PATENT DOCUMENTS

| JP | H07-41468 | | 2/1995 |
|---|---|---|---|
| JP | H08510479 | A | 11/1996 |
| JP | H10511098 | A | 10/1998 |
| JP | H11-503418 | A | 3/1999 |
| JP | 2001031636 | A | 2/2001 |
| JP | 2007008957 | A | 1/2007 |
| WO | WO-1993-15045 | A1 | 8/1993 |
| WO | WO-1995-19952 | | 7/1995 |
| WO | WO-9630014 | A1 | 10/1996 |
| WO | WO-9746511 | A1 | 12/1997 |
| WO | WO-9912902 | A1 | 3/1999 |
| WO | WO-1999-016783 | | 4/1999 |
| WO | WO-0185684 | A1 | 11/2001 |
| WO | WO-2004-013082 | | 2/2004 |
| WO | WO-2006-113837 | | 10/2006 |
| WO | WO-2006105215 | A2 | 10/2006 |
| WO | WO-2007-038372 | A1 | 4/2007 |
| WO | WO-2007-079593 | | 7/2007 |
| WO | WO-2007-79593 | A | 7/2007 |
| WO | WO-2007-120528 | A2 | 10/2007 |
| WO | WO-2009-045479 | | 4/2009 |
| WO | WO-2009-045479 | A1 | 4/2009 |
| WO | WO 2009045479 | A1 * | 4/2009 |
| WO | WO-2011-003103 | | 1/2011 |

OTHER PUBLICATIONS

Mata et al., "Isomerization and Oxidation of Vitamin A in Cone-Dominant Retinas: A Novel Pathway for Visual-Pigment Regeneration in Daylight," *Neuron* 36:69-80 (2002).
Morisette et al., "High-throughput crystallization: polymorphs, salts, co-crystals, and solvates of pharmaceutical solids," *Advanced Drug Delivery Reviews* 56:275-300 (2004).
PCT/US08/011421 Search Report dated Dec. 23, 2008.
PK 1163/2008 Search Report dated Sep. 5, 2009.
Radu et al. "Treatment with isotretinoin inhibits lipofuscin accumulation in a mouse model of recessive Stargardt's macular degeneration." *PNAS*, Apr. 15, 2003, 100(8):4742-4747.
Sieving et al. "Inhibition of the visual cycle in vivo by 13-cis retinoic acid protects from light damage and provides a mechanism for night blindness in isotretinoin therapy." *PNAS*, Feb. 13, 2003, 98(4):1835-1840.
Stella, "Prodrugs as therapeutics," *Expert Opin Ther Patents* 14(3):277-280 (2004).
Testa, "Prodrug research: futile or fertile?" *Biochem Pharmacol* 68:2097-2106 (2004).
Vippagunta et al., "Crystalline Solids," *Advanced Drug Delivery Reviews* 48:3-26 (2001).
Wolff et al., "Burger's Medicinal Chemistry", 5$^{th}$ ed., vol. 1, pp. 975-977 (1994).
NZ584599 Examination Report dated Dec. 19, 2010.
CA2701116 Exam Report dated Sep. 19, 2011.
ID-W0020101071 Office Action dated Oct. 18, 2011.
KR20107009950 Notice of Preliminary Rejection dated Nov. 16, 2011.
MXa2010003667 Office Action dated Nov. 11, 2011.
CL29512008 Office Action dated Feb. 2, 2012.
PCT/US08/011421 IPRP and Written Opinion dated Apr. 7, 2010.
Chandler. "Progress in the Development of ACU-4429 for the Treatment of Dry AMD." 10th Internatl Symp Ocular Pharmacol Therap, Final Program, Dec. 2011, [online] [retrieved on Feb. 17, 2012]. Retrieved the the Internet: http://www.isopt.net/isopt2011/images/abstracts/Chandler%20-%20ACU-4429%20for%20Dry%20AMD.pdf.
Twitter entry for @DrRyo [online], posted Nov. 23, 2011, 9:00 am PST [retrieved on Feb. 17, 2012], Retrieved from the internet: www.twitter.com.
"Experimental Treatments for Macular Degeneration." [online] *The New York Times: Consults, Experts on the Front Lines of Medicine*, Sep. 21, 2011, [retrieved on Feb. 17, 2012], Retrieved from the Internet: http://consults.blogs.nytimes.com/2011/09/21/experimental-treatments-for-macular-degeneration/.
Dr. Ryo. "A Great Opportunity to Tell the ACU-4429 Story." www.drryo.com [online] Jun. 1, 2010 [retrieved on Feb. 17, 2012]. Retrieved from the Internet: http://drryo.com/2010/06/01/a-great-opportunity-to-tell-the-acu-4429-story/.
Dr. Ryo. "A Week to Help Grow Awareness, Understanding of AMD." wwwdrryo.com [online] Sep. 17, 2010 [retrieved Feb. 17, 2012]. Retrieved from the Internet: http://drryo.com/2010/09/17/a-week-to-help-grow-awareness-understanding-of-amd/.
Dr. Ryo. "Acucela's Focus on Diabetic Eye Disease." www.drryo.com [online] Nov. 24, 2009 [retrieved on Feb. 17, 2012]. Retrieved from the Internet: http://drryo.com/2009/11/24/acucela%e2%80%99s-focus-on-diabetic-eye-disease/.
Dr. Ryo. "Blinding Eye Disease Treatments on the Horizon." www.drryo.com [online] Oct. 26, 2009 [retrieved on Feb. 17, 2012]. Retrieved from the Internet: http://drryo.com/2009/10/26/blinding-eye-disease-treatments-on-the-horizon/.
Dr. Ryo. "Charting a New Course . . ." www.drryo.com [online] Aug. 28, 2009 [retrieved on Feb. 17, 2012]. Retrieved from the Internet: http://drryo.com/2009/08/28/new-course/.
Dr. Ryo. "Diabetic Retinopathy 101." www.drryo.com [online] Nov. 19, 2009 [retrieved on Feb. 17, 2012]. Retrieved from the Internet: http://drryo.com/2009/11/19/diabetic-retinopathy-101/.
Dr. Ryo. "ENVISION-ing the Future of Dry-AMD Treatment." www.drryo.com [online] Feb. 23, 2010 [retrieved on Feb. 17, 2012]. Retrieved from the internet: http://drryo.com/2010/02/23/envision-ing-the-future-of-dry-amd-treatment/.
Dr. Ryo. "New Paper Shares First Demonstrated Effect of VCM Treatment on Retinopathy." www.drryo.com [online] Aug. 12, 2010 [retrieved on Feb. 17, 2012]. Retrieved from the Internet: http://drryo.com/2010/08/12/new-paper-shares-first-demonstrated-effect-of-vcm-treatment-on-retinopathy/.
Dr. Ryo. "On the FDA 'Fast Track': ACU-4429: On the FDA 'Fast Track'." wwwdrryo.com [online] May 12, 2010 [retrieved on Feb. 17, 2012]. Retrieved from the Internet: http://drryo.com/2010/05/12/acu-4429-on-the-fda-"fast-track"/.
Dr. Ryo. "Retina Paper Highlights Progress in the Fight Against AMD." wwwdrryo.com [online] Apr. 26, 2011 [retrived on Feb. 17, 2012]. Retrived from the Internet: http://drryo.com/2011/04/26/retina-paper-highlights-progress-in-the-fight-against-amd/.
Dr. Ryo. "Thanks for Your Interest in our 'ENVISION Clarity' Clinical Trial." www.drryo.com [online] Mar. 11, 2010 [retrieved on Feb. 17, 2012]. Retrieved from the Internet: http://drryo.com/2010/03/11/thanks-for-your-interest-in-our-"envision-clarity"-clinical-trial/.
Dr. Ryo. "Visual Cycle Modulation (VCM) 101." www.drryo.com [online] Sep. 4, 2009 [retrieved on Feb. 17, 2012]. Retrieved from the Internet: http://drryo.com/2009/09/04/vcm-101/.
Dr. Ryo. "Why Chickens See Better Colors Than Us and What It Means for AMD?" www.drryo.com [online] Jul. 20, 2010 [retrieved on Feb. 17, 2012]. Retrieved from the Internet: http://drryo.com/2010/07/20/why-chickens-see-better-colors-than-us-and-what-it-means-for-amd/.
"Envision Clarity Trial" 2010 [online] [retrieved on Feb. 16, 2012]. Retrieved from the Internet: http://www.envisiontrial.com, Acucela, Inc.
"Acucela to Present ACU-4429 Phase 1 Data at the 10$^{th}$ International Symposium on Ocular Pharmacology and Therapeutics." www.businesswire.com [online] Nov. 30, 2011 [retrieved on Feb. 17, 2012]. Retrieved from the Internet: www.businesswire.com/news/home/20111130005347/en.
"Acucela to Present Update on AcU-4429 at the Annual Retina International Scientific & Medical Advisory Board Meeting." www.drugs.com [online] May 2010 [retrieved on Feb. 17, 2012]. Retrieved from the Internet: www.drugs.com/clinical_trials/acucela-present-update-acu-4429-annual-retina-international-scientific-medical-advisory-board-9297.html.
PCT/US2010/40983 International Search Report and Written Opinion dated Mar. 31, 2011.
U.S. Appl. No. 13/291,932 Office Action dated Aug. 15, 2012.
U.S. Appl. No. 13/111,679 Office Action dated May 9, 2012.

(56) References Cited

OTHER PUBLICATIONS

U.S. Appl. No. 13/620,388, filed Feb. 1, 2013, Scott et al.
Chemical Encyclopedia, scientific publishing house, Big Russian Encyclopedia, Moscow, 1985, vol. 4, p. 380, col. 752.
CN200880119621 Office Action dated Jan. 23, 2013.
EP10794836.6 Extended Search Report dated Nov. 28, 2012.
EP08832784.6 Extended Search Report dated Nov. 23, 2012.
Maeda A., et al., "Effects of potent inhibitors of the retinoid cycle on visual function and photoreceptor protection from light damage in mice," Molecular Pharmacology, American Society for Pharmacology and Experimental Therapeutics, vol. 70, No. 4, Oct. 1, 2006, p. 1220-1229.
N.A. Tyukavina, Yu I. Baukov, Bio Organic Chemistry, DROFA, M. 2005, p. 83-85.
Prasad P.S., et al. "Age-related macular degeneration: Current and novel therapies," Maturitas, Elservier Science Publishers, Ireland Ltd., vol. 66, No. 1, May 1, 2012, pp. 46-50, XP027009958, ISSN: 0378-5122; retrieved on Apr. 15, 2010.
RU2010117740 Office Action dated Oct. 29, 2012.
U.S. Appl. No. 13/291,932 Office Action dated Mar. 6, 2013.
U.S. Appl. No. 13/111,679 Final Office Action dated Sep. 25, 2012.
U.S. Appl. No. 13/291,948 Office Action dated Sep. 5, 2012.
U.S. Appl. No. 13/291,948 Final Office Action dated Mar. 14, 2013.
AU20132000956 Exam Report dated Apr. 3, 2014.
JP 2010-527992 Office Action dated Aug. 15, 2014.
Kano et al. Formation of dibenzo[b,f]azecines by the reaction of 1-halogeno-phenethyl-1H-2-benzazepines with dimsylsodium. Chemical & Pharmaceutical Bulletin 25(11):2875-2881 (1977).
U.S. Appl. No. 13/111,679 Final Office Action dated Mar. 21, 2014.
U.S. Appl. No. 13/291,932 Office Action dated May 23, 2014.
U.S. Appl. No. 13/291,948 Final Office Action dated May 19, 2014.
VN1-2010-01133 Office Action dated May 31, 2014.
EG 529/2010 Office Action dated Jan. 3, 2014.
IL203317 Office Action dated Oct. 13, 2013.
NZ584599 Examination Report dated Jun. 11, 2012.
NZ584599 Examination Report & Notice of Acceptance of Complete Specification dated Jun. 25, 2012.
Saari et al. (Synthesis and Norepinephrine Depleting Activity of Some Metaralninol Ethers, Journal of Medicinal Chemistry, vol. 13, No. 6, pp. 1057-1061, 1970).
UAa201005512 Office Action dated Jan. 27, 2014 (w/English translation).
U.S. Appl. No. 12/287,039 Office Action dated Jan. 20, 2011.
U.S. Appl. No. 13/111,679 Office Action dated Dec. 4, 2013.
U.S. Appl. No. 13/291,932 Office Action dated Oct. 23, 2013.
U.S. Appl. No. 13/291,948 Office Action dated Dec. 2, 2013.
U.S. Appl. No. 13/620,388 Office Action dated Dec. 5, 2013.
JP 2010-527992 Office Action dated Sep. 3, 2013.
Co-pending U.S. Appl. No. 14/631,763, filed Feb. 25, 2015.
Co-pending U.S. Appl. No. 14/631,779, filed Feb. 25, 2015.
Kucklaender et al. Investigations on the formation of 6-hydroxyindole in the nenitzescu reaction. II. Cyclization of N-(quinonylalkyl)enaminone derivatives. Chemische Berichte 122(8):1493-1498 (1989) (English Abstract).
Wittig et al. Dopamine/Serotonin Receptor Ligands. 9.1 Oxygen-Containing Midsized Heterocyclic Ring Systems and Nonrigidized Analogues. A Step toward Dopamine D5 Receptor Selectivity. Journal of Medicinal Chemistry 47:4155-8, Supporting Information p. S1-S8 (2004).
STN RN 1025987-12-5 (2008).
U.S. Appl. No. 14/631,763 Office Action dated Jan. 26, 2016.
U.S. Appl. No. 14/631,779 Office Action dated Jan. 8, 2016.
Aucela to Present Update on ACU-4429 at the Annual Retina International Scientific & Medical Advisory Board Meeting. www.drugs.com [online] May 2010 [retrieved on Feb. 17, 2012]. Retrieved from the Internet: www.drugs.com/clinical_trials/acucela-present-update-acu-4429-annual-retina-international-scientific-medical-advisory-board-9297.html (3 pgs.).
Co-pending U.S. Appl. No. 16/043,019, filed Jul. 23, 2018.

\* cited by examiner

Figure 6

|  | Day 1<br>% Inhibition | Day 2<br>% Inhibition |
|---|---|---|
| 20mg | 55.3 ± 12.0 | 45.3 ± 18.8 |
| 40mg | 78.6 ± 7.7 | 88.3 ± 5.3 |
| 60mg | 75.4 ± 8.4 | 95.8 ± 2.2 |
| 75mg | 73.5 ± 6.6 | 98.1 ± 0.9 |

Figure 8

| ERG | % Inhibition | STE |
|---|---|---|
| Day 1 | 73.7 | ±6.6 |
| Day 2 | 98.1 | ± 0.93 |
| Day 4 | 18.9* | ± 11.7 |
| Day 7 | -0 | ± 25.5 |

\* Not significantly different from baseline, p = 0.126

*Analysis of averaged ERG values done off-line (in parallel or after completion of ERG after dosing)

Figure 12

| Cohort | Dose | Day 1 | Day 2 | Day 4 | Day 7 |
|---|---|---|---|---|---|
| 3 | 20 mg | 64% ± 43% | 62% ± 45% | n/a | 15% ± 11% |
| 4 | 20 mg | 70% ± 21% | 66% ± 32% | n/a | -7% ± 31% |
| 5 | 40 mg | 79% ± 23% | 88% ± 15% | n/a | 4% ± 10% |
| 6 | 60 mg | 75% ± 20% | 96% ± 5% | n/a | 7% ± 18% |
| 7 | 75 mg | 74% ± 7% | 98% ± 1% | 19% ± 12% | -0% ± 26% |
| 8 | 10 mg | 40% ± 15% | 41% ± 14% | 16% ± 10% | n/a |

PHARMACOLOGY OF VISUAL CYCLE MODULATORS

CROSS REFERENCE

This application claims the benefit of U.S. Provisional Application No. 61/222,875, filed Jul. 2, 2009, and U.S. Provisional Application No. 61/266,922, filed Dec. 4, 2009, each of which is incorporated herein by reference in its entirety.

BACKGROUND OF THE INVENTION

Neurodegenerative diseases, such as glaucoma, macular degeneration, and Alzheimer's disease, affect millions of patients throughout the world. The loss of quality of life associated with these diseases is considerable.

SUMMARY OF THE INVENTION

In one aspect is a method of treating an ophthalmic disease or disorder comprising administration of a non-retinoid compound resulting in a normalized electroretinogram response from about 5% to about 55% after about 12 hours to about 48 hours post administration of said non-retinoid compound. In another aspect is the method wherein the normalized electroretinogram response is from about 5% to about 15%. In another aspect is the method wherein the normalized electroretinogram response is from about 15% to about 25%. In another aspect is the method wherein the normalized electroretinogram response is from about 25% to about 35%. In another aspect is the method wherein the normalized electroretinogram response is from about 35% to about 55%. In another aspect is the method wherein the normalized electroretinogram response is determined after about 12 hours to about 16 hours post administration of said non-retinoid compound. In another aspect is the method wherein the normalized electroretinogram response is determined after about 2 hours to about 12 hours post administration of said non-retinoid compound. In another aspect is the method wherein the normalized electroretinogram response is determined after about 16 hours to about 20 hours post administration of said non-retinoid compound. In another aspect is the method wherein the normalized electroretinogram response is determined after about 20 hours to about 24 hours post administration of said non-retinoid compound. In another aspect is the method wherein the normalized electroretinogram response is determined after about 24 hours to about 30 hours post administration of said non-retinoid compound. In another aspect is the method wherein the normalized electroretinogram response is determined after about 30 hours to about 36 hours post administration of said non-retinoid compound. In another aspect is the method wherein the normalized electroretinogram response is determined after about 36 hours to about 42 hours post administration of said non-retinoid compound. In another aspect is the method wherein the normalized electroretinogram response is determined after about 42 hours to about 48 hours post administration of said non-retinoid compound.

In one aspect is a method of treating an ophthalmic disease or disorder comprising administration of a single dose of a non-retinoid compound resulting in a greater normalized electroretinogram response on day 1 than on day 2.

In one aspect is a method of treating an ophthalmic disease or disorder comprising administration of a non-retinoid compound resulting in a greater therapeutic response on day 2 than on day 1 after the administration of a single dose.

In another aspect is the method wherein the therapeutic response is determined by electroretinography.

In one aspect is a method of treating an ophthalmic disease or disorder comprising administration of a non-retinoid compound resulting in a normalized electroretinogram response less than about 50% for a time period of about 4 hours to about 36 hours after the plasma concentration of said non-retinoid compound has declined to 0.3 $C_{max}$. In one aspect is the method wherein said time period is about 4 hours to about 10 hours. In one aspect is the method wherein said time period is about 10 hours to about 16 hours. In one aspect is the method wherein said time period is about 16 hours to about 24 hours. In one aspect is the method wherein said time period is about 24 hours to about 36 hours. In another aspect is the method wherein the non-retinoid compound is orally administered. In another aspect is the method wherein the non-retinoid compound is administered in the morning. In another aspect is the method wherein the non-retinoid compound is administered upon waking from sleep. In another aspect is the method wherein the non-retinoid compound is administered upon waking from sleep in the morning.

In another aspect is the method wherein the wherein the non-retinoid compound is selected from a compound of Formula (I) or a tautomer, stereoisomer, geometric isomer or pharmaceutically acceptable solvate, hydrate, salt, polymorph, N-oxide or prodrug thereof:

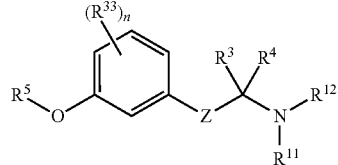

Formula (I)

wherein,

Z is a bond, —C(R$^1$)(R$^2$)—, —C(R$^9$)(R$^{10}$)—C(R$^1$)(R$^2$)—, —X—C(R$^{31}$)(R$^{32}$)—, —C(R$^9$)(R$^{10}$)—C(R$^1$)(R$^2$)—C(R$^{36}$)(R$^{37}$)— or —X—C(R$^{31}$)(R$^{32}$)—C(R$^1$)(R$^2$)—;

R$^1$ and R$^2$ are each independently selected from hydrogen, halogen, C$_1$-C$_5$ alkyl, fluoroalkyl, —OR$^6$ or —NR$^7$R$^8$; or R$^1$ and R$^2$ together form an oxo;

R$^{31}$ and R$^{32}$ are each independently selected from hydrogen, C$_1$-C$_5$ alkyl, or fluoroalkyl;

R$^{36}$ and R$^{37}$ are each independently selected from hydrogen, halogen, C$_1$-C$_5$ alkyl, fluoroalkyl, —OR$^6$ or —NR$^7$R$^8$; or R$^{36}$ and R$^{37}$ together form an oxo; or optionally, R$^{36}$ and R$^1$ together form a direct bond to provide a double bond; or optionally, R$^{36}$ and R$^1$ together form a direct bond, and R$^{37}$ and R$^2$ together form a direct bond to provide a triple bond;

R$^3$ and R$^4$ are each independently selected from hydrogen, alkyl, alkenyl, fluoroalkyl, aryl, heteroaryl, carbocyclyl or C-attached heterocyclyl; or R$^3$ and R$^4$ together with the carbon atom to which they are attached, form a carbocyclyl or heterocyclyl; or R$^3$ and R$^4$ together form an imino;

R$^5$ is C$_1$-C$_{15}$ alkyl, carbocyclyalkyl, arylalkyl, heteroaryl alkyl or heterocyclylalkyl;

$R^7$ and $R^8$ are each independently selected from hydrogen, alkyl, carbocyclyl, heterocyclyl, —C(=O)$R^{13}$, SO$_2R^{13}$, CO$_2R^{13}$ or SO$_2$N$R^{24}R^{25}$; or $R^7$ and $R^8$ together with the nitrogen atom to which they are attached, form an N-heterocyclyl;

X is —O—, —S—, —S(=O)—, —S(=O)$_2$—, —N($R^{30}$)—, —C(=CH$_2$)—, —C(=N—N$R^{35}$)—, or —C(=N—O$R^{35}$)—;

$R^9$ and $R^{10}$ are each independently selected from hydrogen, halogen, alkyl, fluoroalkyl, —O$R^{19}$, —N$R^{20}R^{21}$ or carbocyclyl; or $R^9$ and $R^{10}$ form an oxo; or optionally, $R^9$ and $R^1$ together form a direct bond to provide a double bond; or optionally, $R^9$ and $R^1$ together form a direct bond, and $R^{10}$ and $R^2$ together form a direct bond to provide a triple bond;

$R^{11}$ and $R^{12}$ are each independently selected from hydrogen, alkyl, carbocyclyl, —C(=O)$R^{23}$, —C(NH)NH$_2$, SO$_2R^{23}$, CO$_2R^{23}$ or SO$_2$N$R^{28}R^{29}$; or $R^{11}$ and $R^{12}$, together with the nitrogen atom to which they are attached, form an N-heterocyclyl;

each $R^{13}$, $R^{22}$ and $R^{23}$ is independently selected from alkyl, heteroalkyl, alkenyl, aryl, aralkyl, carbocyclyl, heteroaryl or heterocyclyl;

$R^6$, $R^{19}$, $R^{30}$, $R^{34}$ and $R^{35}$ are each independently hydrogen or alkyl;

$R^{20}$ and $R^{21}$ are each independently selected from hydrogen, alkyl, carbocyclyl, heterocyclyl, —C(=O)$R^{22}$, SO$_2R^{22}$, CO$_2R^{22}$ or SO$_2$N$R^{26}R^{27}$; or $R^{20}$ and $R^{21}$ together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

each $R^{33}$ is independently selected from halogen, O$R^{34}$, alkyl, or fluoroalkyl; and n is 0, 1, 2, 3, or 4.

In another aspect is the method wherein the compound of Formula (I) has the structure of Formula (II):

Formula (II)

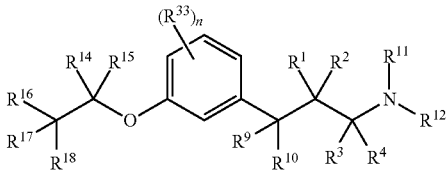

wherein, $R^1$ and $R^2$ are each independently selected from hydrogen, halogen, C$_1$-C$_5$ alkyl, fluoroalkyl, —O—$R^6$ or —N$R^7R^8$; or $R^1$ and $R^2$ together form an oxo;

$R^3$ and $R^4$ are each independently selected from hydrogen or alkyl; or $R^3$ and $R^4$ together form an imino;

$R^7$ and $R^8$ are each independently selected from hydrogen, alkyl, carbocyclyl or —C(=O)$R^{13}$; or $R^7$ and $R^8$, together with the nitrogen atom to which they are attached, form an N-heterocyclyl;

$R^9$ and $R^{10}$ are each independently selected from hydrogen, halogen, alkyl, fluoroalkyl, —O$R^{19}$, —N$R^{20}R^{21}$ or carbocyclyl; or $R^9$ and $R^{10}$ together form an oxo;

$R^{11}$ and $R^{12}$ are each independently selected from hydrogen, alkyl, carbocyclyl or —C(=O)$R^{23}$; or $R^{11}$ and $R^{12}$, together with the nitrogen atom to which they are attached, form an N-heterocyclyl;

each $R^{13}$, $R^{22}$ and $R^{23}$ is independently selected from alkyl, alkenyl, aryl, aralkyl, carbocyclyl, heteroaryl or heterocyclyl;

$R^6$, $R^{19}$ and $R^{34}$ are each independently hydrogen or alkyl;

$R^{20}$ and $R^{21}$ are each independently selected from hydrogen, alkyl, carbocyclyl, —C(=O)$R^{22}$; or $R^{20}$ and $R^{21}$, together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

$R^{14}$ and $R^{15}$ are each independently selected from hydrogen or alkyl;

$R^{16}$ and $R^{17}$ are each independently selected from hydrogen, C$_1$-C$_{13}$ alkyl, halo or fluoroalkyl; or $R^{16}$ and $R^{17}$, together with the carbon to which they are attached form a carbocyclyl;

each $R^{33}$ is independently selected from halogen, O$R^{34}$, alkyl, or fluoroalkyl; and n is 0, 1, 2, 3, or 4; and $R^{18}$ is selected from a hydrogen, alkyl, alkoxy, hydroxy, halo or fluoroalkyl.

In another aspect is the method wherein the compound of Formula (II) is further defined as $R^1$ and $R^2$ are each independently selected from hydrogen, halogen, C$_1$-C$_5$ alkyl, or —O$R^6$;

$R^9$ and $R^{10}$ are each independently selected from hydrogen, halogen, alkyl, or —O$R^{19}$; or $R^9$ and $R^{10}$ together form an oxo;

$R^6$ and $R^{19}$ are each independently hydrogen or alkyl;

$R^{16}$ and $R^{17}$, together with the carbon to which they are attached form a carbocyclyl; and $R^{18}$ is selected from a hydrogen, alkoxy or hydroxy.

In another aspect is the method wherein the compound of Formula (II) is further defined as $R^{16}$ and $R^{17}$, together with the carbon to which they are attached, form a cyclobutyl, cyclopentyl, cyclohexyl, cycloheptyl, or cyclooctyl, and $R^{18}$ is hydrogen or hydroxy.

In another aspect is the method wherein the compound of Formula (II) is (R)-3-amino-1-(3-(cyclohexylmethoxy)phenyl)propan-1-ol.

In another aspect is the method for treating an ophthalmic disease or disorder comprising administration of a non-retinoid compound wherein the non-retinoid compound, or tautomer, stereoisomer, geometric isomer, pharmaceutically acceptable solvate, hydrate, salt, polymorph, N-oxide or prodrug thereof, is selected from the group consisting of:

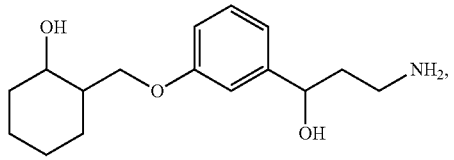

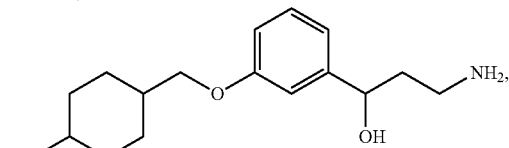

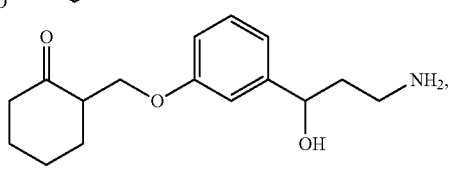

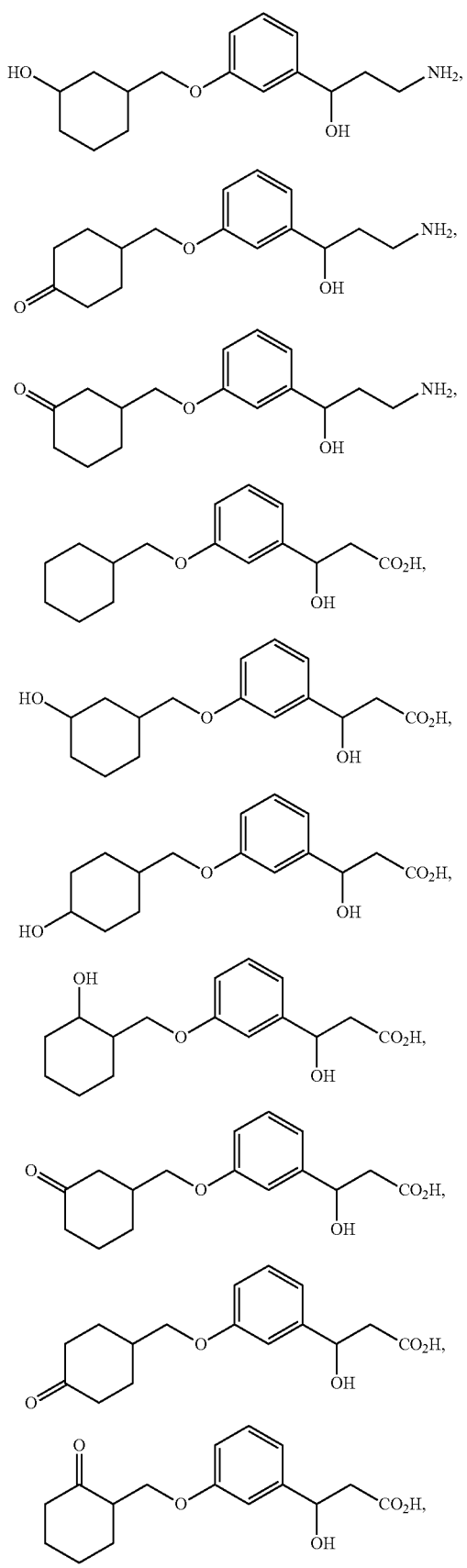

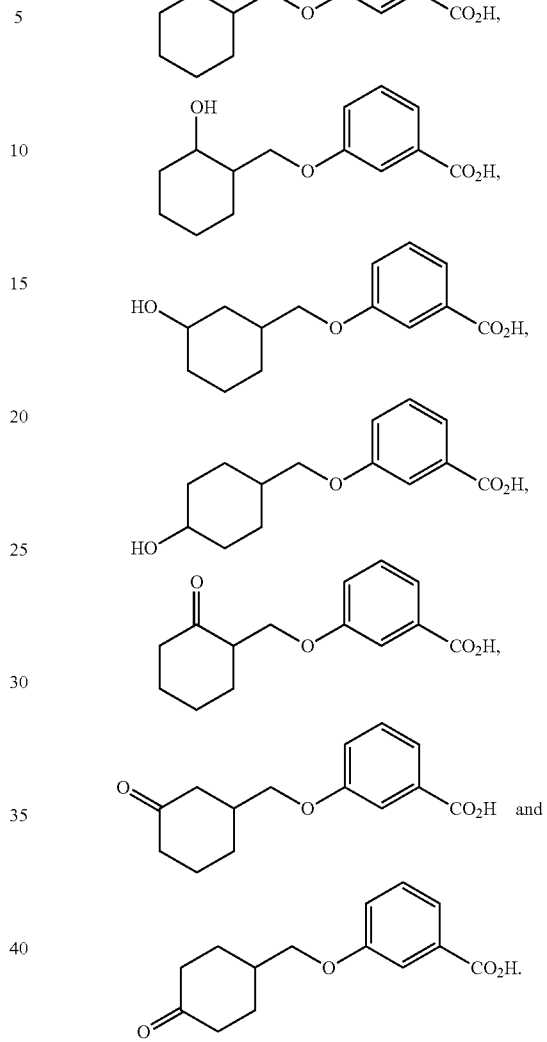

In another aspect is the method wherein the dose is from about 4 mg to about 100 mg. In another aspect is the method wherein the dose is about 75 mg. In another aspect is the method wherein the dose is about 60 mg. In another aspect is the method wherein the dose is about 40 mg.

In another aspect is the method wherein the dose is about 20 mg. In another aspect is the method wherein the dose is about 7 mg. In another aspect is the method wherein the dose is about 5 mg.

In one aspect is the method of determining the dose to be administered for the treatment of an ophthalmic disease or disorder by administration of a non-retinoid visual cycle modulator comprising determining the normalized electroretinogram response from about 12 hours to about 48 hours after the administration of a single dose of said non-retinoid visual cycle modulator. In another aspect is the method of determining the dose to be administered for the treatment of an ophthalmic disease or disorder by administration of a non-retinoid visual cycle modulator comprising determining the normalized electroretinogram response from about 2 hours to about 12 hours after the administration of a single dose of said non-retinoid visual cycle modulator.

In one aspect is a controlled-release solid dosage form for the treatment of an ophthalmic disease or disorder comprising a compound of Formula (I) wherein the plasma $T_{max}$ is observed 12 hours post-dose.

In one aspect is a dosing schedule for the treatment of an ophthalmic disease or disorder comprising a drug holiday after from about 3 months of continuous daily dosing to about 12 months of continuous daily dosing. In another aspect is a dosing schedule wherein the drug holiday is a time period of from about 3 days to about 21 days. In another aspect is a dosing schedule wherein the drug holiday is a time period of from about 1 month to about 2 months.

In another aspect is the method wherein the ophthalmic disease or disorder is selected from retinal detachment, hemorrhagic retinopathy, retinitis pigmentosa, cone-rod dystrophy, Sorsby's fundus dystrophy, optic neuropathy, inflammatory retinal disease, diabetic retinopathy, diabetic maculopathy, retinal blood vessel occlusion, retinopathy of prematurity, ischemia reperfusion related retinal injury, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, myopia, and a retinal disorder associated with AIDS. In another aspect is the method wherein the ophthalmic disease or disorder is age-related macular degeneration or Stargardt's macular dystrophy. In another aspect is the method wherein the ophthalmic disease or disorder is dry age-related macular degeneration. In another aspect is the method wherein the ophthalmic disease or disorder is diabetic retinopathy.

One embodiment provides the compound, or tautomer, stereoisomer, geometric isomer, pharmaceutically acceptable solvate, hydrate, salt, polymorph, N-oxide or prodrug thereof, selected from:

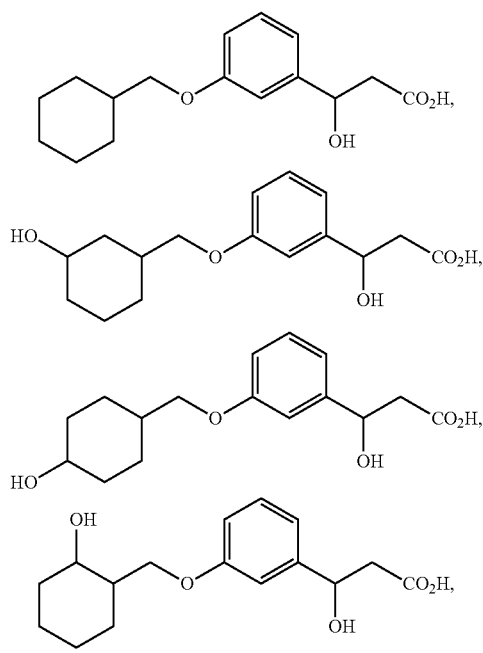

-continued

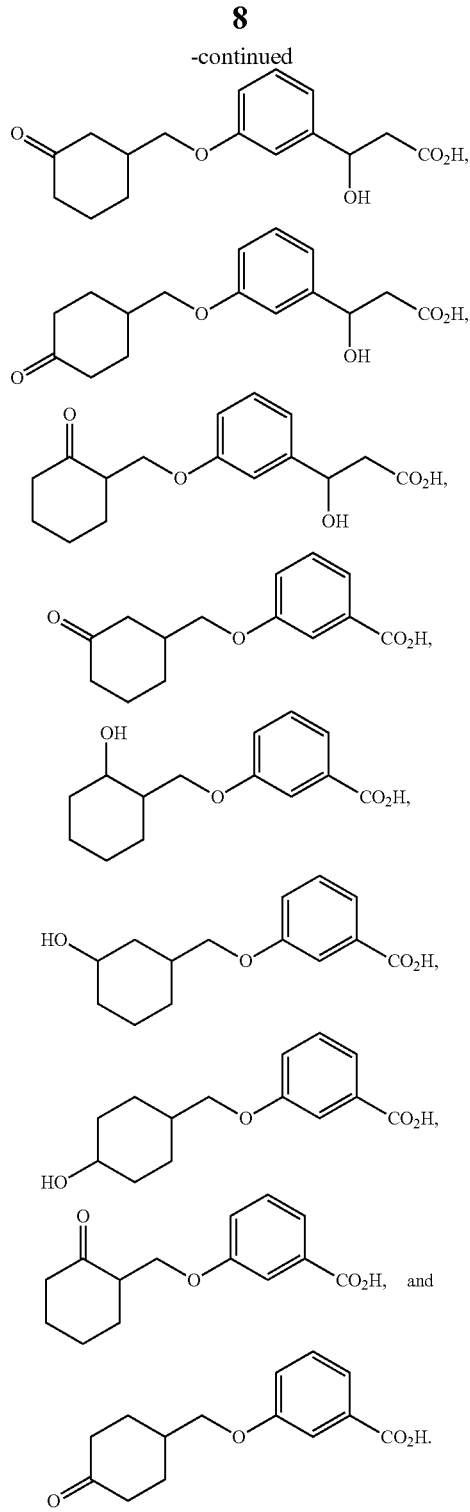

INCORPORATION BY REFERENCE

All publications and patent applications mentioned in this specification are herein incorporated by reference for the purposes cited.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings.

FIG. 3(a) is for the 20 mg dose; FIG. 3(b) is for the 40 mg dose; and FIG. 3(c) is for the 60 mg dose.

FIG. 6 provides an illustrative table comparing the inhibition of normalized EGR response after 30 minutes of retinal illumination vs single oral dose of (R)-3-amino-1-(3-(cyclohexylmethoxy)phenyl)propan-1-ol. Day 1 measurements were obtained at 4 hours post dose and day 2 measurements were obtained at 24 hours post dose.

FIG. 8 provides an illustrative table comparing the inhibition of normalized EGR response after 30 minutes of retinal illumination vs length of time after administration of a single 75 mg oral dose of (R)-3-amino-1-(3-(cyclohexylmethoxy)phenyl)propan-1-ol. Day 1 measurements were obtained at 4 hours post dose and day 2 measurements were obtained at 24 hours post dose.

FIG. 12 provides a summary of the ERG suppression data obtained as described in Example 1.

DETAILED DESCRIPTION OF THE INVENTION

Figure 1:
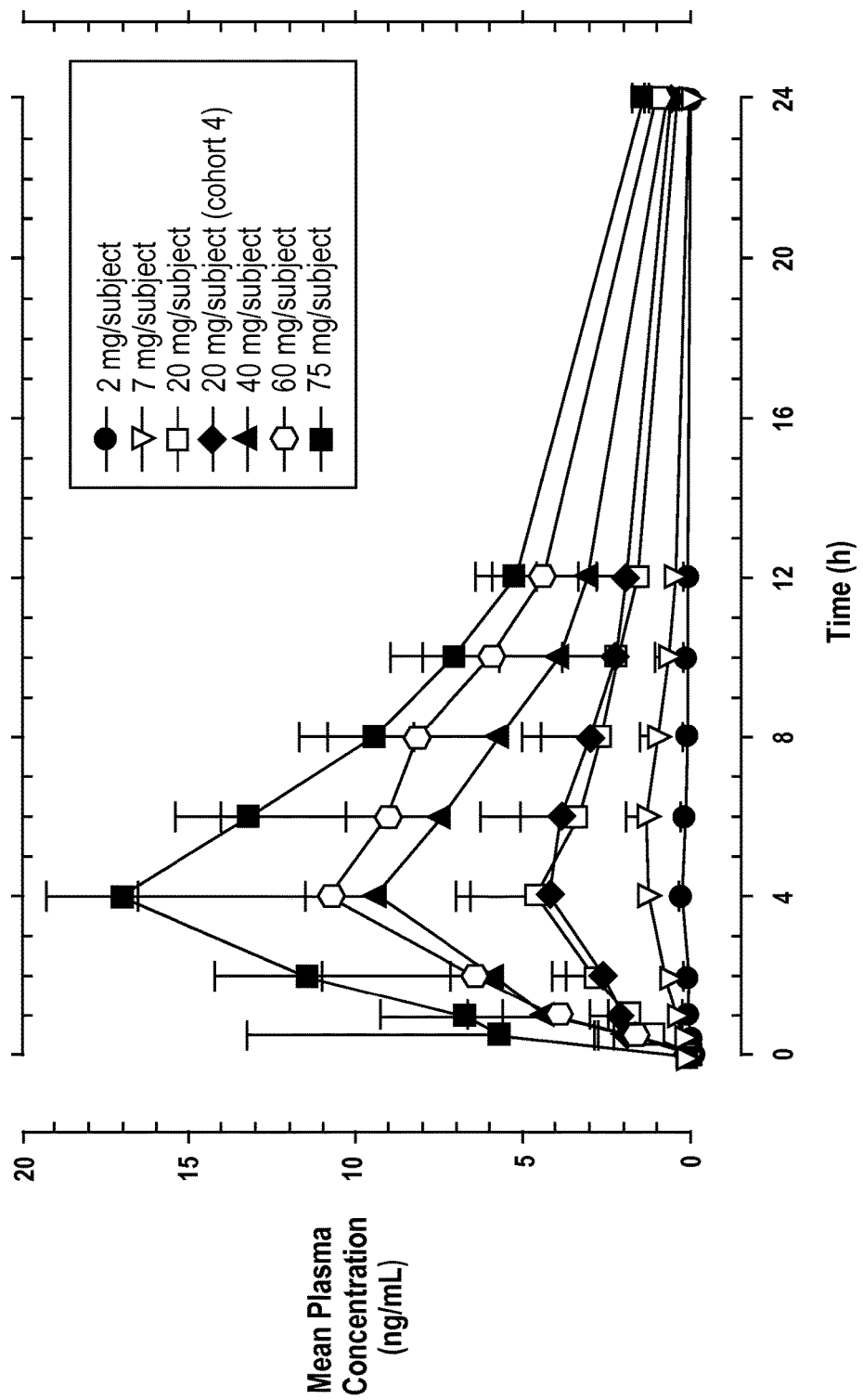
FIG. 1 provides an illustrative linear scale plot of plasma concentration of (R)-3-amino-1-(3-(cyclohexylmethoxy) phenyl)propan-1-ol vs time after administration of a single oral dose.

We recognize a need for an effective treatment for treating ophthalmic diseases or disorders resulting in ophthalmic dysfunction including those described above. In particular, we recognize a need for compositions and methods for treating Stargardt's disease and age-related macular degeneration (AMD) without causing further unwanted side effects such as progressive retinal degeneration, LCA-like conditions, achromatopsia, night blindness or delayed dark adaptation, or systemic vitamin A deficiency. We also recognize a need for effective treatments for other ophthalmic diseases and disorders that adversely affect the retina.

Age-related macular degeneration (AMD) affects between ten and fifteen million patients in the United States, and it is the leading cause of blindness in aging populations worldwide. AMD affects central vision and causes the loss of photoreceptor cells in the central part of retina called the macula. Macular degeneration can be classified into two types: dry-form and wet-form. The dry-form is more common than the wet; about 90% of age-related macular degeneration patients are diagnosed with the dry-form. The wet-form of the disease and geographic atrophy, which is the end-stage phenotype of dry-form AMD, causes the most serious vision loss. All patients who develop wet-form AMD are believed to previously have developed dry-form AMD for a prolonged period of time. The exact causes of AMD are still unknown. The dry-form of AMD may result from the senescence and thinning of macular tissues associated with the deposition of pigment in the macular retinal pigment epithelium. In wet-form AMD, new blood vessels grow beneath the retina, form scar tissue, bleed, and leak fluid. The overlying retina can be severely damaged, creating "blind" areas in the central vision.

For the vast majority of patients who have the dry-form of AMD, no effective treatment is yet available. Because the dry-form of AMD precedes development of the wet-form of AMD, therapeutic intervention to prevent or delay disease progression in the dry-form AMD would benefit patients with dry-form of AMD and might reduce the incidence of the wet-form of AMD.

Decline of vision noticed by the patient or characteristic features detected by an ophthalmologist during a routine eye exam may be the first indicator of AMD. The formation of "drusen," or membranous debris beneath the retinal pigment epithelium of the macula is often the first physical sign that AMD is developing. Late symptoms include the perceived distortion of straight lines and, in advanced cases, a dark, blurry area or area with absent vision appears in the center of vision; and/or there may be color perception changes.

Different forms of genetically-linked macular degenerations may also occur in younger patients. In other maculopathies, factors in the disease are heredity, nutritional, traumatic, infection, or other ecologic factors.

Glaucoma is a broad term used to describe a group of diseases that causes a slowly progressive visual field loss, usually asymptomatically. The lack of symptoms may lead to a delayed diagnosis of glaucoma until the terminal stages of the disease. The prevalence of glaucoma is estimated to be 2.2 million in the United States, with about 120,000 cases of blindness attributable to the condition. The disease is particularly prevalent in Japan, which has four million reported cases. In many parts of the world, treatment is less accessible than in the United States and Japan, thus glaucoma ranks as a leading cause of blindness worldwide. Even if subjects afflicted with glaucoma do not become blind, their vision is often severely impaired.

The progressive loss of peripheral visual field in glaucoma is caused by the death of ganglion cells in the retina. Ganglion cells are a specific type of projection neuron that connects the eye to the brain. Glaucoma is usually accompanied by an increase in intraocular pressure. Current treatment includes use of drugs that lower the intraocular pressure; however, contemporary methods to lower the intraocular pressure are often insufficient to completely stop disease progression. Ganglion cells are believed to be susceptible to pressure and may suffer permanent degeneration prior to the lowering of intraocular pressure. An increasing number of cases of normal-tension glaucoma are observed in which ganglion cells degenerate without an observed increase in the intraocular pressure. Current glaucoma drugs only treat intraocular pressure and are ineffective in preventing or reversing the degeneration of ganglion cells.

Recent reports suggest that glaucoma is a neurodegenerative disease, similar to Alzheimer's disease and Parkinson's disease in the brain, except that it specifically affects retinal neurons. The retinal neurons of the eye originate from diencephalon neurons of the brain. Though retinal neurons are often mistakenly thought not to be part of the brain, retinal cells are key components of the central nervous system, interpreting the signals from the light-sensing cells.

Alzheimer's disease (AD) is the most common form of dementia among the elderly. Dementia is a brain disorder that seriously affects a person's ability to carry out daily activities. Alzheimer's is a disease that affects four million people in the United States alone. It is characterized by a loss of nerve cells in areas of the brain that are vital to memory and other mental functions. Currently available drugs can ameliorate AD symptoms for a relatively finite period of time, but no drugs are available that treat the disease or completely stop the progressive decline in mental function. Recent research suggests that glial cells that support the neurons or nerve cells may have defects in AD sufferers, but the cause of AD remains unknown. Individuals with AD seem to have a higher incidence of glaucoma and age-related macular degeneration, indicating that similar pathogenesis may underlie these neurodegenerative diseases of the eye and brain. (See Giasson et al., *Free Radic. Biol. Med.* 32:1264-75 (2002); Johnson et al., *Proc. Natl. Acad. Sci. USA* 99:11830-35 (2002); Dentchev et al., *Mol. Vis.* 9:184-90 (2003)).

Neuronal cell death underlies the pathology of these diseases. Unfortunately, very few compositions and methods that enhance retinal neuronal cell survival, particularly photoreceptor cell survival, have been discovered. A need therefore exists to identify and develop compositions that can be used for treatment and prophylaxis of a number of retinal diseases and disorders that have neuronal cell death as a primary, or associated, element in their pathogenesis.

In vertebrate photoreceptor cells, the irradiance of a photon causes isomerization of 11-cis-retinylidene chromophore to all-trans-retinylidene and uncoupling from the visual opsin receptors. This photoisomerization triggers conformational changes of opsins, which, in turn, initiate the biochemical chain of reactions termed phototransduction (Filipek et al., *Annu. Rev. Physiol.* 65:851-79 (2003)). Regeneration of the visual pigments requires that the chromophore be converted back to the 11-cis-configuration in the processes collectively called the retinoid (visual) cycle (see, e.g., McBee et al., *Prog. Retin. Eye Res.* 20:469-52 (2001)). First, the chromophore is released from the opsin and reduced in the photoreceptor by retinol dehydrogenases. The product, all-trans-retinol, is trapped in the adjacent retinal pigment epithelium (RPE) in the form of insoluble fatty acid esters in subcellular structures known as retinosomes (Imanishi et al., *J. Cell Biol.* 164:373-87 (2004)).

In Stargardt's disease (Allikmets et al., *Nat. Genet.* 15:236-46 (1997)), a disease associated with mutations in the ABCR transporter that acts as a flippase, the accumulation of all-trans-retinal may be responsible for the formation of a lipofuscin pigment, A2E, which is toxic towards retinal pigment epithelial cells and causes progressive retinal degeneration and, consequently, loss of vision (Mata et al., *Proc. Natl. Acad. Sci. USA* 97:7154-59 (2000); Weng et al., *Cell* 98:13-23 (1999)). Treating patients with an inhibitor of retinol dehydrogenases, 13-cis-RA (Isotretinoin, Accutane®, Roche), has been considered as a therapy that might prevent or slow the formation of A2E and might have protective properties to maintain normal vision (Radu et al., *Proc. Natl. Acad. Sci. USA* 100:4742-47 (2003)). 13-cis-RA has been used to slow the synthesis of 11-cis-retinal by inhibiting 11-cis-RDH (Law et al., *Biochem. Biophys. Res. Commun.* 161:825-9 (1989)), but its use can also be associated with significant night blindness. Others have proposed that 13-cis-RA works to prevent chromophore regeneration by binding RPE65, a protein essential for the isomerization process in the eye (Gollapalli et al., *Proc. Natl. Acad. Sci. USA* 101:10030-35 (2004)). Gollapalli et al. reported that 13-cis-RA blocked the formation of A2E and suggested that this treatment may inhibit lipofuscin accumulation and, thus, delay either the onset of visual loss in Stargardt's disease or age-related macular degeneration, which are both associated with retinal pigment-associated lipofuscin accumulation. However, blocking the retinoid cycle and forming unliganded opsin may result in more severe consequences and worsening of the patient's prognosis (see, e.g., Van Hooser et al., *J. Biol. Chem.* 277:19173-82 (2002); Woodruff et al., *Nat. Genet.* 35:158-164 (2003)). Failure of the chromophore to form may lead to progressive retinal degeneration and may produce a phenotype similar to Leber Congenital Amaurosis (LCA), which is a very rare genetic condition affecting children shortly after birth.

Definitions

As used in the specification and appended claims, unless specified to the contrary, the following terms have the meaning indicated:

As used herein and in the appended claims, the singular forms "a," "and," and "the" include plural referents unless the context clearly dictates otherwise. Thus, for example, reference to "a compound" includes a plurality of such compounds, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.

"Thioxo" refers to the =S radical.

"Imino" refers to the =N—H radical.

"Hydrazino" refers to the =N—NH$_2$ radical.

"Alkyl" refers to a straight or branched hydrocarbon chain radical consisting solely of carbon and hydrogen atoms, containing no unsaturation, having from one to fifteen carbon atoms (e.g., C$_1$-C$_{15}$ alkyl). In certain embodiments, an alkyl comprises one to thirteen carbon atoms (e.g., C$_1$-C$_{13}$ alkyl). In certain embodiments, an alkyl comprises one to eight carbon atoms (e.g., C$_1$-C$_8$ alkyl). In other embodiments, an alkyl comprises five to fifteen carbon atoms (e.g., C$_5$-C$_{15}$ alkyl). In other embodiments, an alkyl comprises five to eight carbon atoms (e.g., C$_5$-C$_8$ alkyl). The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. Unless stated otherwise specifically in the specification, an alkylene chain is optionally substituted by one or more of the following substituents: halo, cyano, nitro, aryl, cycloalkyl, heterocyclyl, heteroaryl, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S)O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain is optionally substituted by one or more of the following substituents: halo, cyano, nitro, aryl, cycloalkyl, heterocyclyl, heteroaryl, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OF$^a$ (where t is 1 or 2) and —S(O)$_t$N(R$^a$)$_2$ (where t is 1 or 2) where each R$^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless otherwise indicated.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. Aryl groups include, but are not limited to, groups such as phenyl, fluorenyl, and naphthyl. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—$N(R^a)_2$, —$R^b$—C(O)$R^a$, —$R^b$—C(O)O$R^a$, —$R^b$—C(O)$N(R^a)_2$, —$R^b$—O—$R^c$—C(O)$N(R^a)_2$, —$R^b$—$N(R^a)$C(O)O$R^a$, —$R^b$—$N(R^a)$C(O)$R^a$, —$R^b$—$N(R^a)$S(O)$_t R^a$ (where t is 1 or 2), —$R^b$—S(O)$_t OR^a$ (where t is 1 or 2) and —$R^b$—S(O)$_t N(R^a)_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula —$R^c$-aryl where $R^c$ is an alkylene chain as defined above, for example, benzyl, diphenylmethyl and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non-aromatic monocyclic or polycyclic hydrocarbon radical consisting solely of carbon and hydrogen atoms, which may include fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$SR^a$, —$R^b$—OC(O)—$R^a$, —$R^b$—$N(R^a)_2$, —$R^b$—C(O)$R^a$, —$R^b$—C(O)O$R^a$, —$R^b$—C(O)$N(R^a)_2$, —$R^b$—O—$R^c$—C(O)$N(R^a)_2$, —$R^b$—$N(R^a)$C(O)O$R^a$, —$R^b$—$N(R^a)$C(O)$R^a$, —$R^b$—$N(R^a)$S(O)$_t R^a$ (where t is 1 or 2), —$R^b$—S(O)$_t OR^a$ (where t is 1 or 2) and —$R^b$—S(O)$_t N(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$SR^a$, —$R^b$—OC(O)—$R^a$, —$R^b$—$N(R^a)_2$, —$R^b$—C(O)$R^a$, —$R^b$—C(O)O$R^a$, —$R^b$—C(O)N$(R^a)_2$, —$R^b$—O—$R^c$—C(O)$N(R^a)_2$, —$R^b$—$N(R^a)$C(O)O$R^a$, —$R^b$—$N(R^a)$C(O)$R^a$, —$R^b$—$N(R^a)$S(O)$_t R^a$ (where t is 1 or 2), —$R^b$—(O)$_t OR^a$ (where t is 1 or 2) and —$R^b$—S(O)$_t N(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$SR^a$, —$R^b$—OC(O)—$R^a$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

The compounds, or their pharmaceutically acceptable salts may contain one or more asymmetric centers and may thus give rise to enantiomers, diastereomers, and other stereoisomeric forms that may be defined, in terms of absolute stereochemistry, as (R)— or (S)— or, as (D)- or (L)- for amino acids. When the compounds described herein contain olefinic double bonds or other centers of geometric asymmetry, and unless specified otherwise, it is intended that the compounds include both E and Z geometric isomers (e.g., cis or trans.) Likewise, all possible isomers, as well as their racemic and optically pure forms, and all tautomeric forms are also intended to be included.

A "stereoisomer" refers to a compound made up of the same atoms bonded by the same bonds but having different three-dimensional structures, which are not interchangeable. It is therefore contemplated that various stereoisomers and mixtures thereof and includes "enantiomers," which refers to two stereoisomers whose molecules are nonsuperimposeable mirror images of one another.

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In solutions where tautomerization is possible, a chemical equilibrium of the tautomers will exist. The exact ratio of the tautomers depends on several factors, including temperature, solvent, and pH. Some examples of tautomeric pairs include:

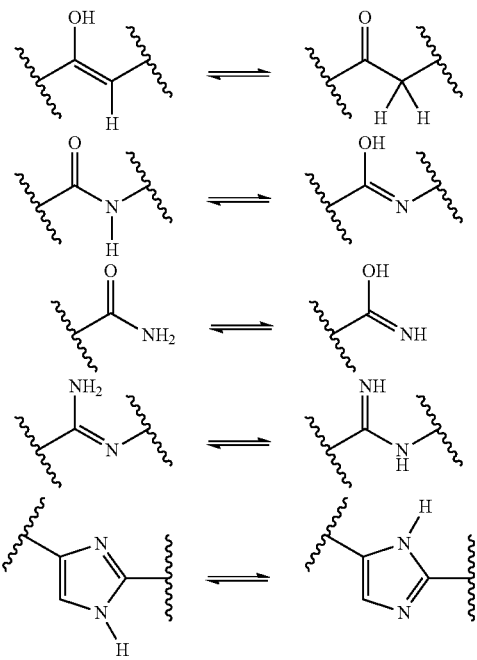

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the alkoxyphenyl-linked amine derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," Journal of Pharmaceutical Science, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Non-retinoid compound" refers to any compound that is not a retinoid. A retinoid is a compound that has a diterpene skeleton possessing a trimethylcyclohexenyl ring and a polyene chain that terminates in a polar end group. Examples of retinoids include retinaldehyde and derived imine/hydrazide/oxime, retinol and any derived ester, retinyl amine and any derived amide, retinoic acid and any derived ester or amide. A non-retinoid compound can comprise though not require an internal cyclic group (e.g., aromatic group). A non-retinoid compound can contain though not require an alkoxyphenyl-linked amine group.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Compounds of the Invention

One embodiment provides the compound, or tautomer, stereoisomer, geometric isomer, pharmaceutically acceptable solvate, hydrate, salt, polymorph, N-oxide or prodrug thereof, selected from:

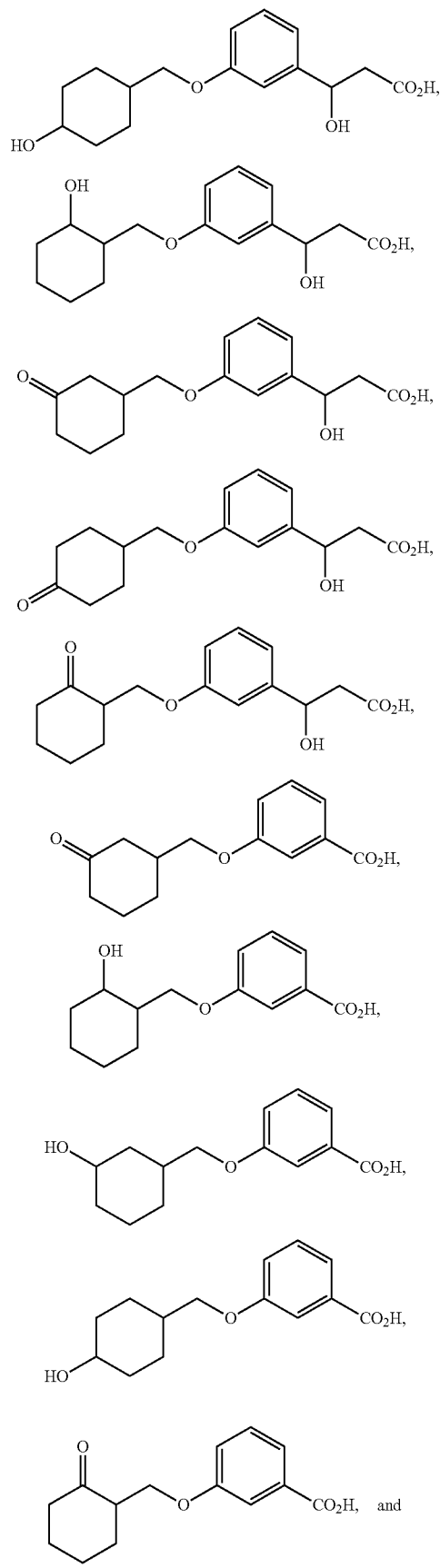

-continued

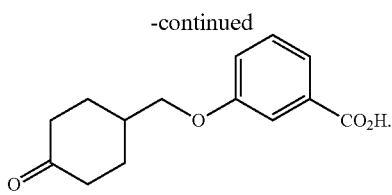

Compositions of the Method

One embodiment provides a method of treating an ophthalmic disease or disorder comprising administration of a compound of Formula (I) or a tautomer, stereoisomer, geometric isomer or pharmaceutically acceptable solvate, hydrate, salt, polymorph, N-oxide or prodrug thereof:

Formula (I)

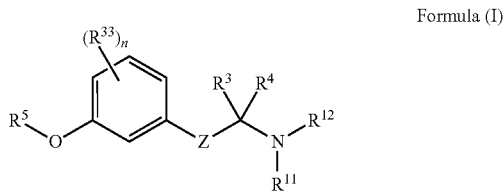

wherein,
- Z is a bond, —C($R^1$)($R^2$)—, —C($R^9$)($R^{10}$)—C($R^1$)($R^2$)—, —X—C($R^{31}$)($R^{32}$)—, —C($R^9$)($R^{10}$)—C($R^1$)($R^2$)—C($R^{36}$)($R^{37}$) or —X—C($R^{31}$)($R^{32}$)—C($R^1$)($R^2$)—;
- $R^1$ and $R^2$ are each independently selected from hydrogen, halogen, $C_1$-$C_5$ alkyl, fluoroalkyl, —$OR^6$ or —$NR^7R^8$; or $R^1$ and $R^2$ together form an oxo;
- $R^{31}$ and $R^{32}$ are each independently selected from hydrogen, $C_1$-$C_5$ alkyl, or fluoroalkyl;
- $R^{36}$ and $R^{37}$ are each independently selected from hydrogen, halogen, $C_1$-$C_5$ alkyl, fluoroalkyl, —$OR^6$ or —$NR^7R^8$; or $R^{36}$ and $R^{37}$ together form an oxo; or optionally, $R^{36}$ and $R^1$ together form a direct bond to provide a double bond; or optionally, $R^{36}$ and $R^1$ together form a direct bond, and $R^{37}$ and $R^2$ together form a direct bond to provide a triple bond;
- $R^3$ and $R^4$ are each independently selected from hydrogen, alkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;
- $R^5$ is $C_1$-$C_{15}$ alkyl, carbocyclyalkyl, arylalkyl, heteroarylalkyl or heterocyclylalkyl;
- $R^7$ and $R^8$ are each independently selected from hydrogen, alkyl, carbocyclyl, heterocyclyl, —C(=O)$R^{13}$, $SO_2R^{13}$, $CO_2R^{13}$ or $SO_2NR^{24}R^{25}$; or $R^7$ and $R^8$ together with the nitrogen atom to which they are attached, form an N-heterocyclyl;
- X is —O—, —S—, —S(=O)—, —S(=O)$_2$—, —N($R^{30}$)—, —C(=$CH_2$)—, —C(=N—$NR^{35}$)—, or —C(=N—$OR^{35}$)—;
- $R^9$ and $R^{10}$ are each independently selected from hydrogen, halogen, alkyl, fluoroalkyl, —$OR^{19}$, —$NR^{20}R^{21}$ or carbocyclyl; or $R^9$ and $R^{10}$ form an oxo; or optionally, $R^9$ and $R^1$ together form a direct bond to provide a double bond; or optionally, $R^9$ and $R^1$ together form a direct bond, and $R^{10}$ and $R^2$ together form a direct bond to provide a triple bond;
- $R^{11}$ and $R^{12}$ are each independently selected from hydrogen, alkyl, carbocyclyl, —C(=O)$R^{23}$, —C(NH)$NH_2$, $SO_2R^{23}$, $CO_2R^{23}$ or $SO_2NR^{28}R^{29}$; or $R^{11}$ and $R^{12}$, together with the nitrogen atom to which they are attached, form an N-heterocyclyl;
- each $R^{13}$, $R^{22}$ and $R^{23}$ is independently selected from alkyl, heteroalkyl, alkenyl, aryl, aralkyl, carbocyclyl, heteroaryl or heterocyclyl;
- $R^6$, $R^{19}$, $R^{30}$, $R^{34}$ and $R^{35}$ are each independently hydrogen or alkyl;
- $R^{20}$ and $R^{21}$ are each independently selected from hydrogen, alkyl, carbocyclyl, heterocyclyl, —C(=O)$R^{22}$, $SO_2R^{22}$, $CO_2R^{22}$ or $SO_2N^{26}R^{27}$; or $R^{20}$ and $R^{21}$ together with the nitrogen atom to which they are attached, form an N-heterocyclyl; and
- each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;
- each $R^{33}$ is independently selected from halogen, $OR^{34}$, alkyl, or fluoroalkyl; and n is 0, 1, 2, 3, or 4.

Another embodiment provides for the method wherein the compound of Formula (I) has the structure of Formula (II):

Formula (II)

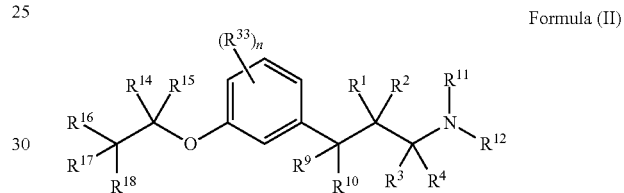

wherein,
- $R^1$ and $R^2$ are each independently selected from hydrogen, halogen, $C_1$-$C_5$ alkyl, fluoroalkyl, —$OR^6$ or —$NR^7R^8$; or $R^1$ and $R^2$ together form an oxo;
- $R^3$ and $R^4$ are each independently selected from hydrogen or alkyl; or $R^3$ and $R^4$ together form an imino;
- $R^7$ and $R^8$ are each independently selected from hydrogen, alkyl, carbocyclyl or —C(=O)$R^{13}$; or $R^7$ and $R^8$, together with the nitrogen atom to which they are attached, form an N-heterocyclyl;
- $R^9$ and $R^{10}$ are each independently selected from hydrogen, halogen, alkyl, fluoroalkyl, —$OR^{19}$, —$NR^{20}R^{21}$ or carbocyclyl; or $R^9$ and $R^{10}$ together form an oxo;
- $R^{11}$ and $R^{12}$ are each independently selected from hydrogen, alkyl, carbocyclyl or —C(=O)$R^{23}$; or $R^{11}$ and $R^{12}$, together with the nitrogen atom to which they are attached, form an N-heterocyclyl;
- each $R^{13}$, $R^{22}$ and $R^{23}$ is independently selected from alkyl, alkenyl, aryl, aralkyl, carbocyclyl, heteroaryl or heterocyclyl;
- $R^6$, $R^{19}$ and $R^{34}$ are each independently hydrogen or alkyl;
- $R^{20}$ and $R^{21}$ are each independently selected from hydrogen, alkyl, carbocyclyl, —C(=O)$R^{22}$; or $R^{20}$ and $R^{21}$, together with the nitrogen atom to which they are attached, form an N-heterocyclyl; and
- each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;
- $R^{14}$ and $R^{15}$ are each independently selected from hydrogen or alkyl;
- $R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl;

each $R^{33}$ is independently selected from halogen, $OR^{34}$, alkyl, or fluoroalkyl; and n is 0, 1, 2, 3, or 4; and
$R^{18}$ is selected from a hydrogen, alkyl, alkoxy, hydroxy, halo or fluoroalkyl.

Another embodiment provides for the method wherein the compound of Formula (II) is further defined as $R^1$ and $R^2$ are each independently selected from hydrogen, halogen, $C_1$-$C_5$ alkyl, or —$OR^6$; $R^9$ and $R^{10}$ are each independently selected from hydrogen, halogen, alkyl, or —$OR^{19}$; or $R^9$ and $R^{10}$ together form an oxo; $R^6$ and $R^{19}$ are each independently hydrogen or alkyl; $R^{16}$ and $R^{17}$, together with the carbon to which they are attached form a carbocyclyl; and $R^{18}$ is selected from a hydrogen, alkoxy or hydroxy.

Another embodiment provides for the method wherein the compound of Formula (II) is further defined as $R^{16}$ and $R^{17}$, together with the carbon to which they are attached, form a cyclobutyl, cyclopentyl, cyclohexyl, cycloheptyl, or cyclooctyl, and $R^{18}$ is hydrogen or hydroxy.

Another embodiment provides for a method wherein the compound of Formula (II) is (R)-3-amino-1-(3-(cyclohexylmethoxy)phenyl)propan-1-ol.

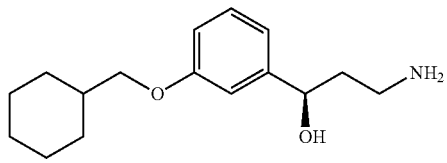 [SMILES: NCC[C@@H](O)c1cccc(OCC2CCCCC2)c1]

(R)-3-amino-1-(3-(cyclohexylmethoxy)phenyl)propan-1-ol

In another aspect is the method for treating an ophthalmic disease or disorder comprising administration of a non-retinoid compound wherein the non-retinoid compound, or tautomer, stereoisomer, geometric isomer, pharmaceutically acceptable solvate, hydrate, salt, polymorph, N-oxide or prodrug thereof, is selected from the group consisting of:

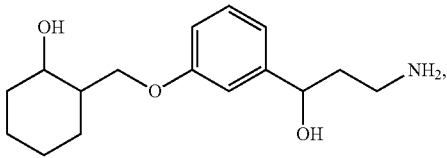

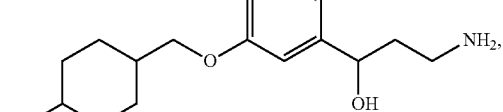

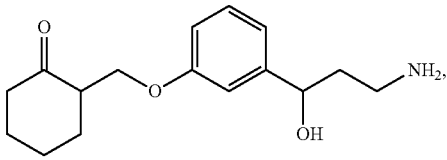

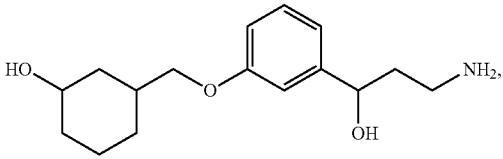

-continued

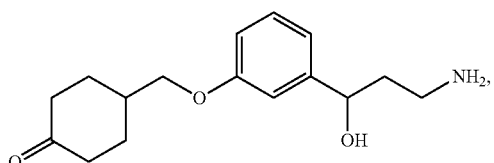

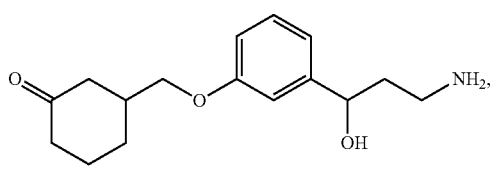

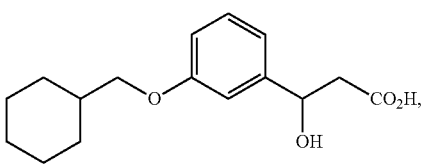

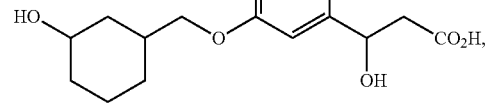

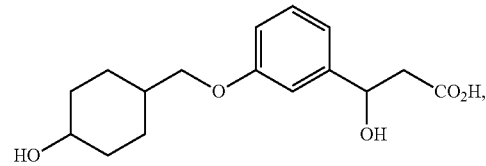

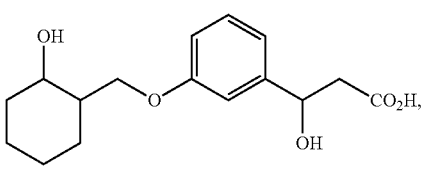

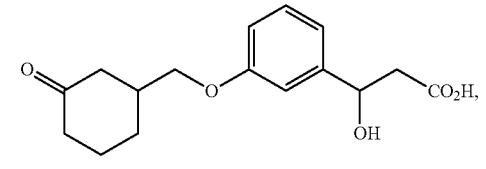

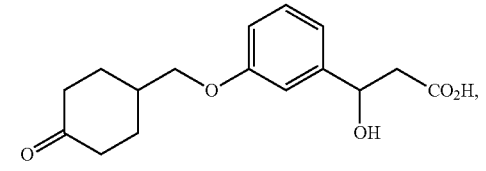

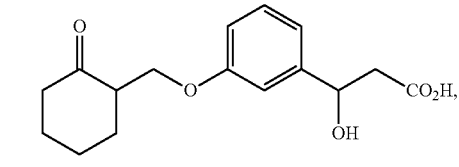

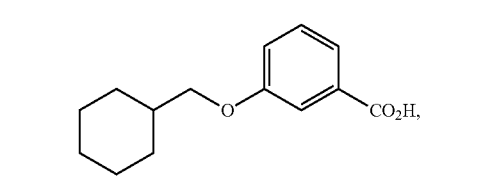

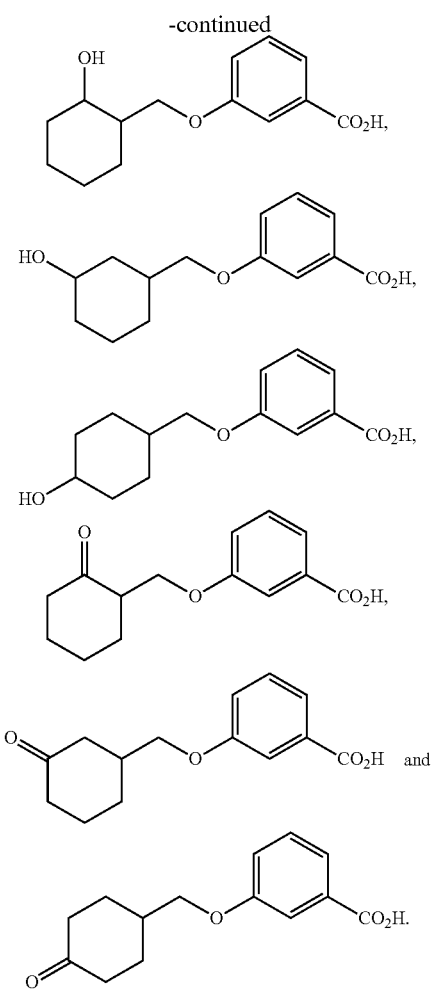

Methods of Treatment

In one aspect is a method of treating an ophthalmic disease or disorder comprising administration of a non-retinoid compound resulting in a normalized electroretinogram response from about 5% to about 55% after about 12 hours to about 48 hours post administration of said non-retinoid compound. In another aspect is the method wherein the normalized electroretinogram response is from about 5% to about 15%. In another aspect is the method wherein the normalized electroretinogram response is from about 15% to about 25%. In another aspect is the method wherein the normalized electroretinogram response is from about 25% to about 35%. In another aspect is the method wherein the normalized electroretinogram response is from about 35% to about 55%. In another aspect is the method wherein the normalized electroretinogram response is determined after about 12 hours to about 16 hours post administration of said non-retinoid compound. In another aspect is the method wherein the normalized electroretinogram response is determined after about 2 hours to about 12 hours post administration of said non-retinoid compound. In another aspect is the method wherein the normalized electroretinogram response is determined after about 16 hours to about 20 hours post administration of said non-retinoid compound. In another aspect is the method wherein the normalized electroretinogram response is determined after about 20 hours to about 24 hours post administration of said non-retinoid compound. In another aspect is the method wherein the normalized electroretinogram response is determined after about 24 hours to about 30 hours post administration of said non-retinoid compound. In another aspect is the method wherein the normalized electroretinogram response is determined after about 30 hours to about 36 hours post administration of said non-retinoid compound. In another aspect is the method wherein the normalized electroretinogram response is determined after about 36 hours to about 42 hours post administration of said non-retinoid compound. In another aspect is the method wherein the normalized electroretinogram response is determined after about 42 hours to about 48 hours post administration of said non-retinoid compound.

In one aspect is a method of treating an ophthalmic disease or disorder comprising administration of a single dose of a non-retinoid compound resulting in a normalized electroretinogram response that is greater on day 1 than on day 2. In another aspect is a method of treating an ophthalmic disease or disorder comprising administration of a non-retinoid compound resulting in a greater therapeutic response on day 2 than on day 1 after the administration of a single dose. In another aspect is the method wherein the therapeutic response is determined by electroretinography.

In one aspect is a method of treating an ophthalmic disease or disorder comprising administration of a non-retinoid compound resulting in a normalized electroretinogram response less than about 50% for a time period of about 4 hours to about 36 hours after the plasma concentration of said non-retinoid compound has declined to 0.3 $C_{max}$.

FIG. 1 illustrates the linear scale plot of plasma concentration of (R)-3-amino-1-(3-(cyclohexylmethoxy)phenyl) propan-1-ol vs time after administration of a single oral dose, thus indicating that this compound of Formula (I) is orally bioavailable over a wide range of dosage amount and has a Cmax of about 4 hours and a $t_{1/2}$ of about 6-7 hours.

Figure 2:
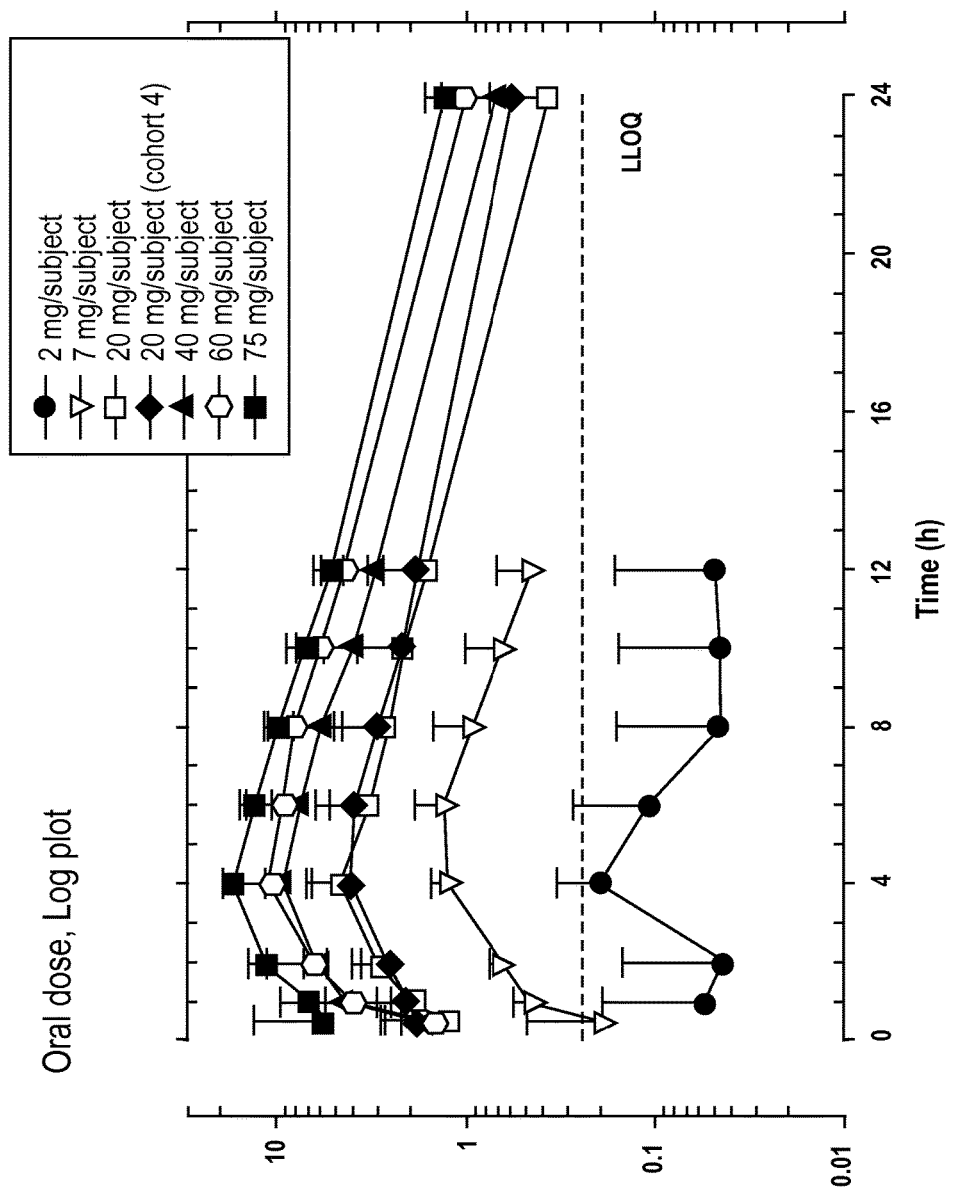
FIG. 2 provides an illustrative log scale plot of plasma concentration of (R)-3-amino-1-(3-(cyclohexylmethoxy) phenyl)propan-1-ol vs time after administration of a single oral dose.

FIG. 2 illustrates the log scale plot of plasma concentration of (R)-3-amino-1-(3-(cyclohexylmethoxy)phenyl)propan-1-ol vs time after administration of a single oral dose.

Figure 3:
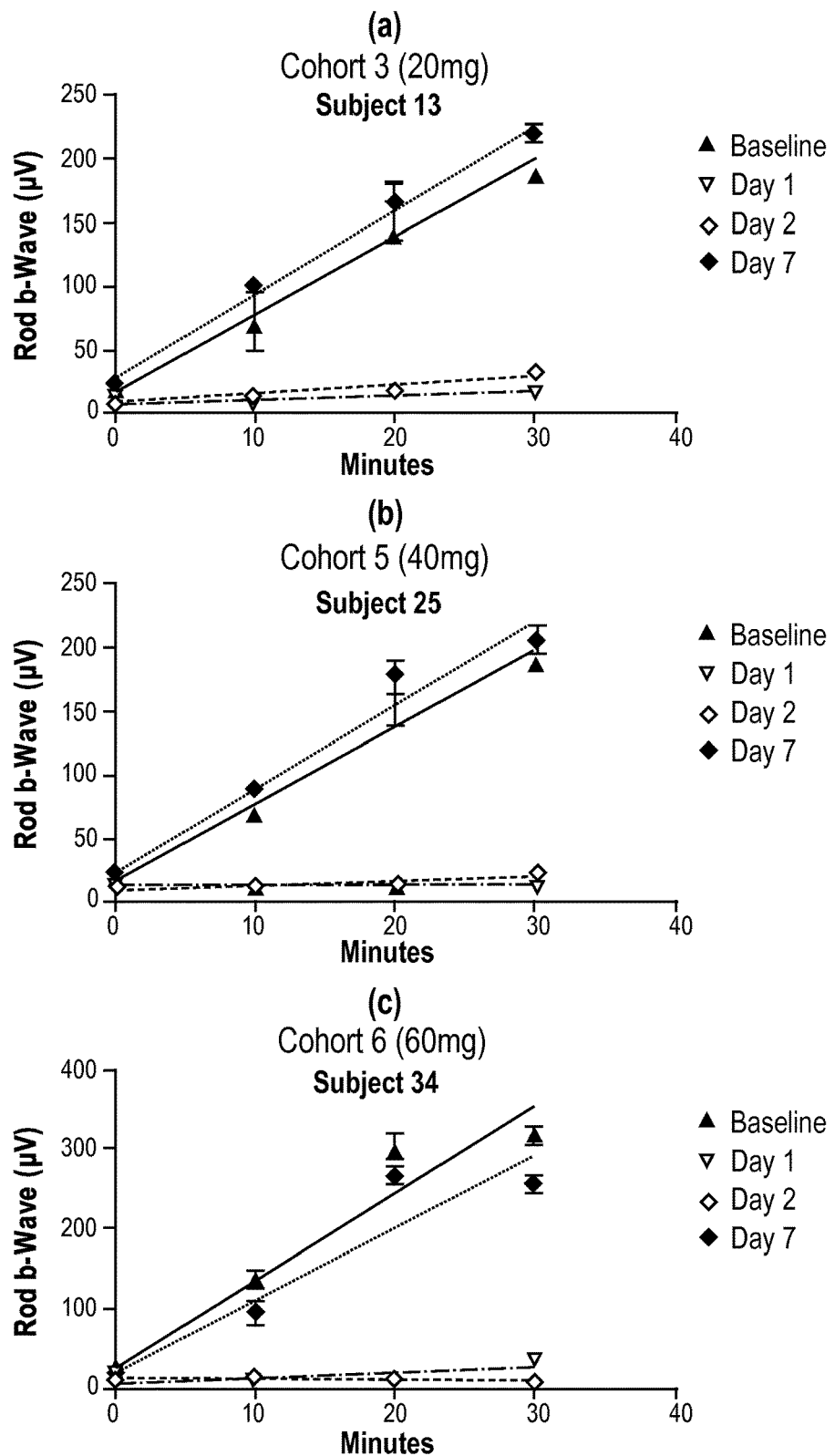
FIG. 3 provides an illustrative single patient EGR response vs retinal illumination time at days 1, 2 and 7, compared to baseline (no drug treatment) after administration of a single oral dose of (R)-3-amino-1-(3-(cyclohexylmethoxy)phenyl)propan-1-ol.

FIG. 3 illustrates the single patient EGR response vs retinal illumination time at days 1, 2 and 7, compared to baseline (no drug treatment) after administration of a single oral dose of (R)-3-amino-1-(3-(cyclohexylmethoxy)phenyl) propan-1-ol. FIG. 3(a) is for the 20 mg dose; FIG. 3(b) is for the 40 mg dose; and FIG. 3(c) is for the 60 mg dose. The EGR determinations for days 1 and 2 were performed at 4 hours and 24 hours post dose, respectively. The EGR determinations clearly indicated a pronounced pharmacodynamic effect at day 2 (24 post dose) that has subsided by day 7. Comparison to blood levels provided in FIGS. 1 and 2 indicate a pharmacodynamic effect with little to no compound in the blood.

Figure 4:
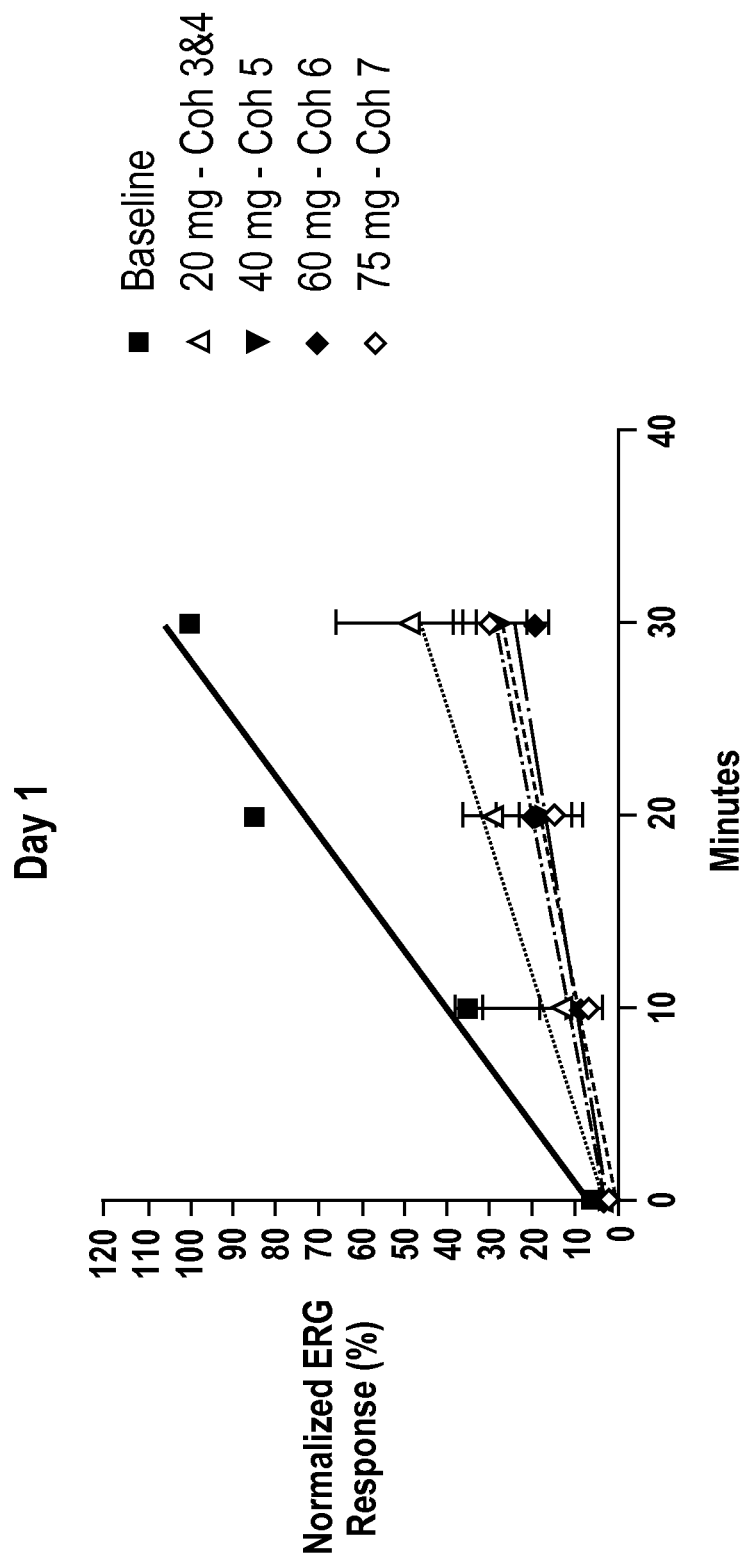
FIG. 4 provides an illustrative normalized EGR response vs retinal illumination time at day 1 (4 hours post dosing), compared to baseline (no drug treatment) after administration of a single oral dose of (R)-3-amino-1-(3-(cyclohexylmethoxy)phenyl)propan-1-ol. The doses examined are 20 mg, 40 mg, 60 mg and 75 mg.
Figure 5:
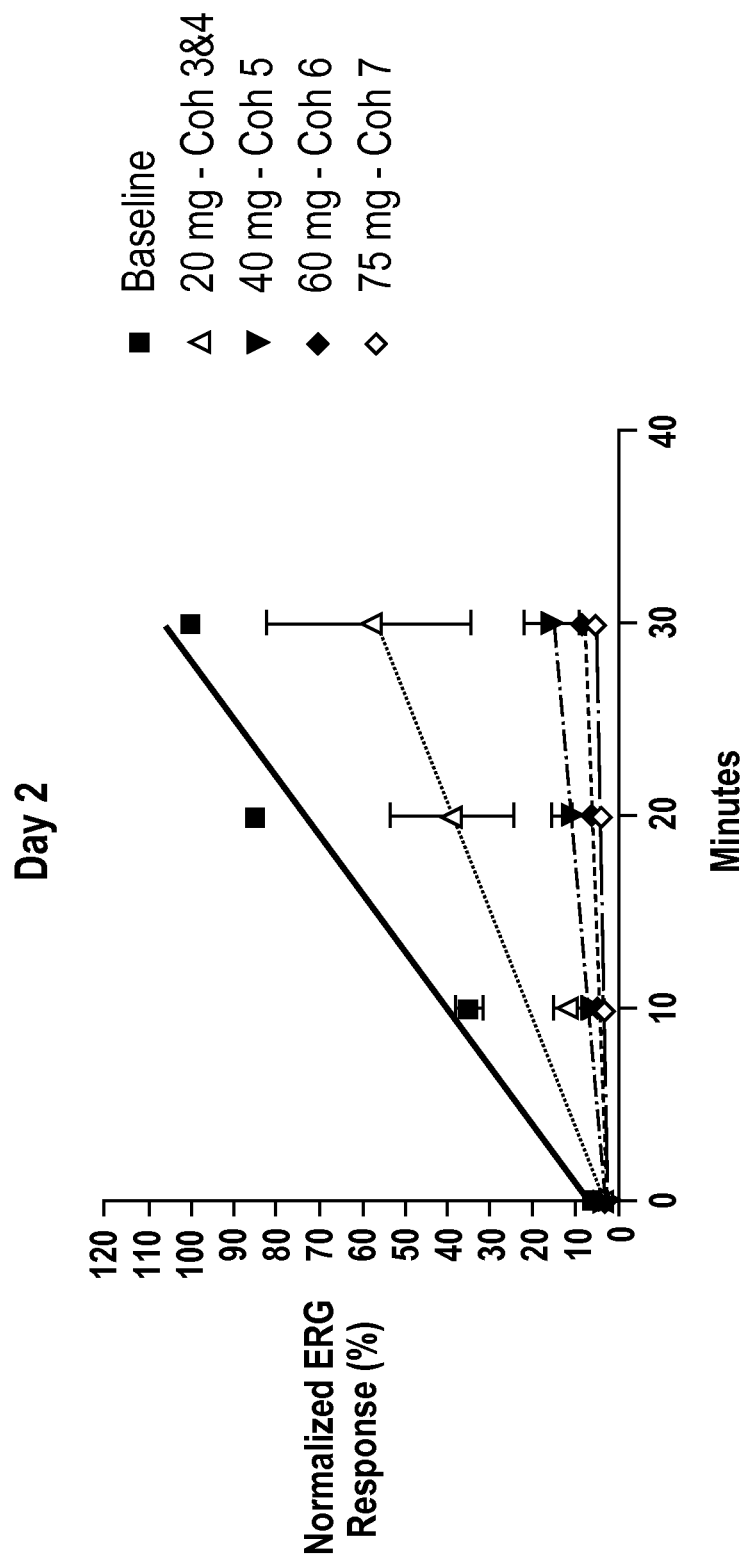
FIG. 5 provides an illustrative normalized EGR response vs retinal illumination time at day 2 (24 hours post dosing), compared to baseline (no drug treatment) after administration of a single oral dose of (R)-3-amino-1-(3-(cyclohexylmethoxy)phenyl)propan-1-ol. The doses examined are 20 mg, 40 mg, 60 mg and 75 mg.

FIG. 4 illustrates the normalized EGR response vs retinal illumination time at day 1 (4 hours post dosing), compared to baseline (no drug treatment) after administration of a single oral dose of (R)-3-amino-1-(3-(cyclohexylmethoxy) phenyl)propan-1-ol. The doses examined are 20 mg, 40 mg, 60 mg and 75 mg. FIG. 5 illustrates the normalized EGR response vs retinal illumination time at day 2 (24 hours post dosing), compared to baseline (no drug treatment) after administration of a single oral dose of (R)-3-amino-1-(3-(cyclohexylmethoxy)phenyl)propan-1-ol. The doses examined are 20 mg, 40 mg, 60 mg and 75 mg. Comparison of FIGS. 4 and 5 indicate that the pharmacological effect is more pronounced on day 2 than on day 1. Comparison to blood levels provided in FIGS. 1 and 2 indicate a pharmacodynamic effect with little to no compound in the blood.

FIG. 6 is a table comparing the inhibition of normalized EGR response after 30 minutes of retinal illumination vs single oral dose of (R)-3-amino-1-(3-(cyclohexylmethoxy) phenyl)propan-1-ol. Day 1 measurements were obtained at 4 hours post dose and day 2 measurements were obtained at 24 hours post dose. Note for comparison to FIGS. 4 and 5 that % inhibition=(100−normalized EGR response).

Figure 7:
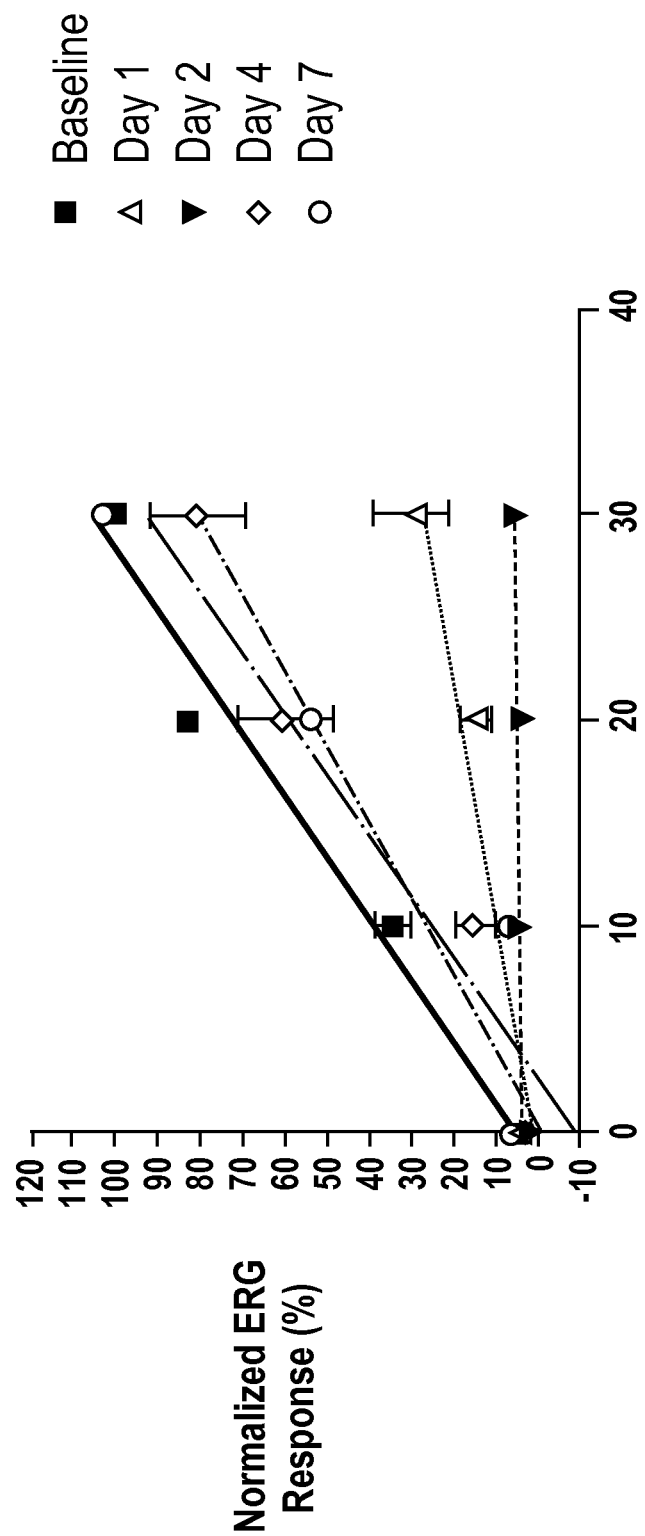
FIG. 7 provides an illustrative normalized EGR response vs retinal illumination time, compared to baseline (no drug treatment) after administration of a single 75 mg oral dose of (R)-3-amino-1-(3-(cyclohexylmethoxy)phenyl)propan-1-ol at 1 day (4 hours post dose), day 2 (24 hours post dose), day 4 and day 7.

FIG. 7 illustrates the normalized EGR response vs retinal illumination time, compared to baseline (no drug treatment) after administration of a single 75 mg oral dose of (R)-3-amino-1-(3-(cyclohexylmethoxy)phenyl)propan-1-ol at 1 day (4 hours post dose), day 2 (24 hours post dose), day 4 and day 7. The data presented in FIG. 7 indicate a pharmacodynamic effect that is greater on day 2 than on day 1 but by day 4 has subsided.

FIG. 8 is a table comparing the inhibition of normalized EGR response after 30 minutes of retinal illumination vs length of time after administration of a single 75 mg oral dose of (R)-3-amino-1-(3-(cyclohexylmethoxy)phenyl)propan-1-ol. Day 1 measurements were obtained at 4 hours post dose and day 2 measurements were obtained at 24 hours post dose. FIG. 8 is a tabular summary of the data presented in FIG. 7. Note for comparison to FIG. 6 that % inhibition= (100−normalized EGR response).

Dosing Schedule

Provided in one embodiment is a method for determining the dose of non-retinoid visual cycle modulator to be administered for the treatment of an ophthalmic disease or disorder comprising determining the normalized electroretinogram response from about 12 hours to about 48 hours after the administration of a single dose of said non-retinoid visual cycle modulator.

In another aspect are dosing schedules (e.g., number of administrations per day) for the treatment of the ophthalmic diseases and conditions described herein. In one embodiment, the compound is administered once daily (which includes multiple sub-doses of the compound administered at approximately the same time); in another embodiment, the compound is administered once every two days (which includes multiple sub-doses of the compound administered at approximately the same time); and in another embodiment, the compound is administered once every three days or more (which includes multiple sub-doses of the compound administered at approximately the same time).

In another aspect are dosing schedules (e.g., variations between dose amounts of subsequent administrations) for the treatment of the ophthalmic diseases and conditions described herein. In one embodiment, the compound is administered on day 1 at a dose level twice that administered on following days (e.g., a loading dose). In another embodiment, the compound is administered on day 1 at a dose level three times that administered on following days.

In another aspect are dosing schedules (e.g., time of day when compound is administered) for the treatment of the ophthalmic diseases and conditions described herein. In one embodiment, the compound is administered in the morning; in another embodiment, the compound is administered in the evening; in another embodiment, the compound is administered upon waking; and in another embodiment, the compound is administered prior to going to sleep. In one embodiment, the compound is administered as a controlled release formulation in the evening. In one embodiment, the compound is administered as a controlled release formulation in the evening prior to going to bed. In another embodiment, the compound is administered prior to eating, or alternatively during a meal, or alternatively subsequent to a meal. In some embodiments, such a meal is breakfast; in other embodiments, such a meal is lunch; in yet other embodiments, such a meal is dinner/supper.

In one aspect the daily dose of (R)-3-amino-1-(3-(cyclohexylmethoxy)phenyl)propan-1-ol is about 4 mg to about 100 mg. In another aspect the daily dose of (R)-3-amino-1-(3-(cyclohexylmethoxy)phenyl)propan-1-ol is about 5 mg; about 7 mg; about 15 mg; about 20 mg; about 40 mg; about 60 mg; about 75 mg; and about 100 mg. In another aspect the daily dose of (R)-3-amino-1-(3-(cyclohexylmethoxy) phenyl)propan-1-ol is about 100 mg; about 150 mg; about 200 mg; about 250 mg; about 300 mg; about 350 mg; and about 400 mg.

Drug Holiday

In certain circumstances, a physician skilled in the art of treating ophthalmic diseases and disorders may, optionally, and temporarily, suspend administration, or alternatively, reduce the dose, of the compound of Formula (I) to effect a drug holiday. One embodiment provides a dosing schedule for the treatment of an ophthalmic disease or disorder comprising a drug holiday after from about 3 months of continuous daily dosing to about 12 months of continuous daily dosing. Another embodiment provides a dosing schedule for the treatment of an ophthalmic disease or disorder comprising a drug holiday wherein the drug holiday is a time period of from about 3 days to about 21 days. Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained.

Controlled Release Formulations

Provided in one embodiment is a controlled release solid dosage formulation for the treatment of an ophthalmic disease or disorder comprising a compound of Formula (I) wherein the plasma $T_{max}$ is observed 12 hours post-dose. In another embodiment the plasma $T_{max}$ is observed 10 hours post-dose. In another embodiment the plasma $T_{max}$ is observed 14 hours post-dose.

Controlled release formulations which provide a delayed release and thus a delayed plasma $T_{max}$ are known to those skilled in the art of pharmaceutical compounding and formulation. The controlled release pharmaceutical preparation described herein comprises a core containing a compound of Formula (I) and a coating layer containing a water-repellent salt and a water-insoluble and slightly water-permeable acrylic polymer having trimethylammoniumethyl group, which surrounds said core. If desired, another coating layer of at least one material selected from the group consisting of ethylcellulose, or hydroxypropylcellulose may be provided around said coating layer.

In the present application, a polymer of acrylic acid, methyl acrylate, ethyl acrylate, methacrylic acid, methyl methacrylate, ethyl methacrylate or the like, which has trimethylammoniumethyl group in the molecule, may be used as a water-insoluble and slightly water-permeable acrylic polymer constituting the coating layer. For instance, a copolymer of ethyl acrylate, methyl methacrylate and β-acryloyloxyethyltrimethylammonium chloride in which about 0.025 to about 0.033 mole of β-acryloyloxyethyltrimethylammonium chloride is contained per mole of the other neutral acrylic monomers is preferably used. Such copolymer is commercially available under trade mark "Eudragit RS" from Rohm Pharma, Germany or the like. The above-mentioned polymer may contain, for instance, a small quantity of a water-permeable polymer. Such copolymer is, for example, commercially available under trade mark "Eudragit RL" from Rohm Pharma, Germany or the like.

As ethylcellulose or hydroxypropylcellulose which is a material of another coating layer provided around the coating layer of an acrylic polymer, for instance, ethylcellulose containing about 46.5 to about 51.0% of ethoxy group, hydroxypropylcellulose containing about 53.4 to about 77.5% of hydroxypropoxy group or the like can be suitably used.

As a water-repellent salt which constitute the coating layer with an acrylic polymer, a salt of higher fatty acid and an alkaline earth metal is preferably used. Examples of the salts are calcium stearate, magnesium stearate and the like.

One embodiment provides, the above-mentioned acrylic polymer and the water-repellent salt in the coating layer in a ratio about 0.5 to about 5 parts by weight. Another embodiment provides the above-mentioned acrylic polymer and the water-repellent salt in the coating layer in a ratio about 1.5 to about 4.5 parts by weight. Another embodiment provides the above-mentioned acrylic polymer and the water-repellent salt in the coating layer in a ratio about 2 to about 4 parts by weight of the acrylic polymer is contained per part by weight of the water-repellent salt.

The amount of the coating layer for the core depends on the form or the size of the core. It is preferable that the amount of the coating layer to be used increase depending on the increase of the surface area per unit weight, that is, the decrease of the particle size of the core. For example, in case of spherical particles having mean particle size of about 500 to about 1000 micrometer, the amount of the coating layer is about 5 to about 80%, preferably about 7 to about 50%, in particular, preferably about 8 to about 30%, based on the weight of the core.

In the present application, the form of the core to be coated is not particularly limited and various forms such as plain tablet, pill, granule and fine granule may be suitably used. Granulated cores having mean particle size of about 300 to about 5000 micrometer, in particular, about 500 to about 1500 micrometer may be used.

In addition, various additives such as an excipient, a binder, a lubricant, an aggregation-preventing agent and a solubilizer may be contained in the core.

Examples of excipients are sugars such as sucrose, lactose, mannitol and glucose, starch, crystalline cellulose, calcium phosphate, calcium sulfate, calcium lactate and the like. Examples of carriers for regulating particle sizes are sucrose, lactose, starch, crystalline cellulose and the like. Examples of binders are polyvinylalcohol, polyacrylic acid, polymethacrylic acid, polyvinylpyrrolidone, glucose, sucrose, lactose, maltose, sorbitol, mannitol, hydroxyethylcellulose, hydroxypropylmethylcellulose, hydroxypropylcellulose, macrogols, arabic gum, gelatin, agar, starch and the like. Examples of lubricants are stearic acid, talc and the like. Examples of aggregation-preventing agents are the above-mentioned lubricants, silicone dioxide, colloidal silicone dioxide and the like. Examples of solubilizers are organic acids such as fumaric acid, succinic acid and malic acid and the like.

The pharmaceutical preparation of the present invention can be prepared by coating cores containing a compound of Formula (I) with a dispersion of a water-insoluble and slightly water-permeable acrylic polymer having trimethylammoniumethyl group and a water-repellent salt. The preparation of the cores can be carried out according to the usual procedure for the preparation, for example, as described in Remingtons Pharmaceutical Sciences 17, 1603-1632, 1633-1643 (Mack Publishing Company, published in 1985). For example, the cores can be prepared by granulating the composition of a medicinal compound, a binder and other additives such as an excipient according to the method of wet oscillating granulation, rotating granulation, fluidizing bed granulation or the like to obtain granules. Alternatively, for example, the cores may be prepared using carriers for regulating particle sizes wherein spherically granulated carriers may be coated with a compound of Formula (I) according to the usual method such as powder coating method to obtain the cores. Powder coating can be carried out, for instance, by gradually adding a compound of Formula (I) and suitable additives such as an excipient with spraying a solution obtained by dissolving a binder in a suitable solvent such as water, a lower alcohol such as methanol, ethanol, propanol, isopropanol or butanol, a lower alkanone such as acetone or methylethylketone, chloroform, dichloromethane, dichloroethane or a mixture thereof, on carrier particles to be cores, according to the method of rotating granulation, pan coating, fluidizing bed coating or the like.

The coating for thus obtained cores can be carried out by adhering a dispersion of a water-repellent salt and an acrylic polymer to the cores followed by drying.

As a dispersion medium for the above-mentioned component of the coating layer, water, an alcohol such as methanol, ethanol or propanol, a ketone such as acetone, a halogenated hydrocarbon such as methylenechloride or chloroform, a mixture thereof or the like is exemplified. Water, an alcohol or a mixture thereof is preferable, and ethanol or a mixture of ethanol and water is particularly preferable.

The coating can be carried out according to a method generally used in the art for preparation such as the method of fluidizing bed coating or pan coating. For example, in case of the method of fluidizing bed coating, the coating can be carried out as follows: the cores are fluidized in an apparatus by means of air pressure, they are spray-coated with an aqueous dispersion of a water-repellent salt and an acrylic acid polymer at an adequate rate from the nozzle of the spray-gun.

The concentration of a water-repellent salt and an acrylic polymer in the dispersion is not particularly limited, but it is preferable that these components are added within the above-mentioned scope of the preferable proportion of both components, to be the concentration of about 5 to about 40% by weight. In addition, a plasticizer, a coloring agent and the like may be contained in the dispersion. As a plasticizer, for instance, triacetin, triethyl citrate, acetyltributyl citrate, diethyl phthalate, polyethyleneglycol, polysorbate or the like can be suitably used. The amount of the plasticizer to be used is preferably about 5 to about 40% by weight based on the weight of an acrylic polymer.

The drying of thus obtained coating layer can be easily carried out, for example, by heating at about 35° C. to about 100° C., particularly about 40° C. to about 70° C.

Thus obtained controlled release pharmaceutical preparation of the present invention may be administered as it is or in a form filled in capsules.

The controlled release pharmaceutical preparation described herein has the following characteristics because of its coating layer of a slightly water-permeable acrylic polymer. That is, a compound of Formula (I) rapidly dissolves from the preparation only after a certain period which depends upon the amount of the coating layer. The time until the start of the dissolution of a compound of Formula (I) is optionally adjustable by changing the amount of the coating layer.

Ophthalmic Disease or Disorder

In one embodiment the ophthalmic disease or disorder is selected from retinal detachment, hemorrhagic retinopathy, retinitis pigmentosa, cone-rod dystrophy, Sorsby's fundus dystrophy, optic neuropathy, inflammatory retinal disease, diabetic retinopathy, diabetic maculopathy, retinal blood vessel occlusion, retinopathy of prematurity, ischemia reperfusion related retinal injury, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, myopia, and a retinal disorder associated with AIDS. In another embodiment, the ophthalmic disease or disorder is age-related macular degeneration or Stargardt's macular dystrophy. In an additional embodiment, the ophthalmic disease or disorder is dry age-related macular degeneration. In an additional embodiment, the ophthalmic disease or disorder is diabetic retinopathy.

EXAMPLES

Example 1—Phase 1A Study of Safety and Pharmacodynamics Effect

Figure 9:
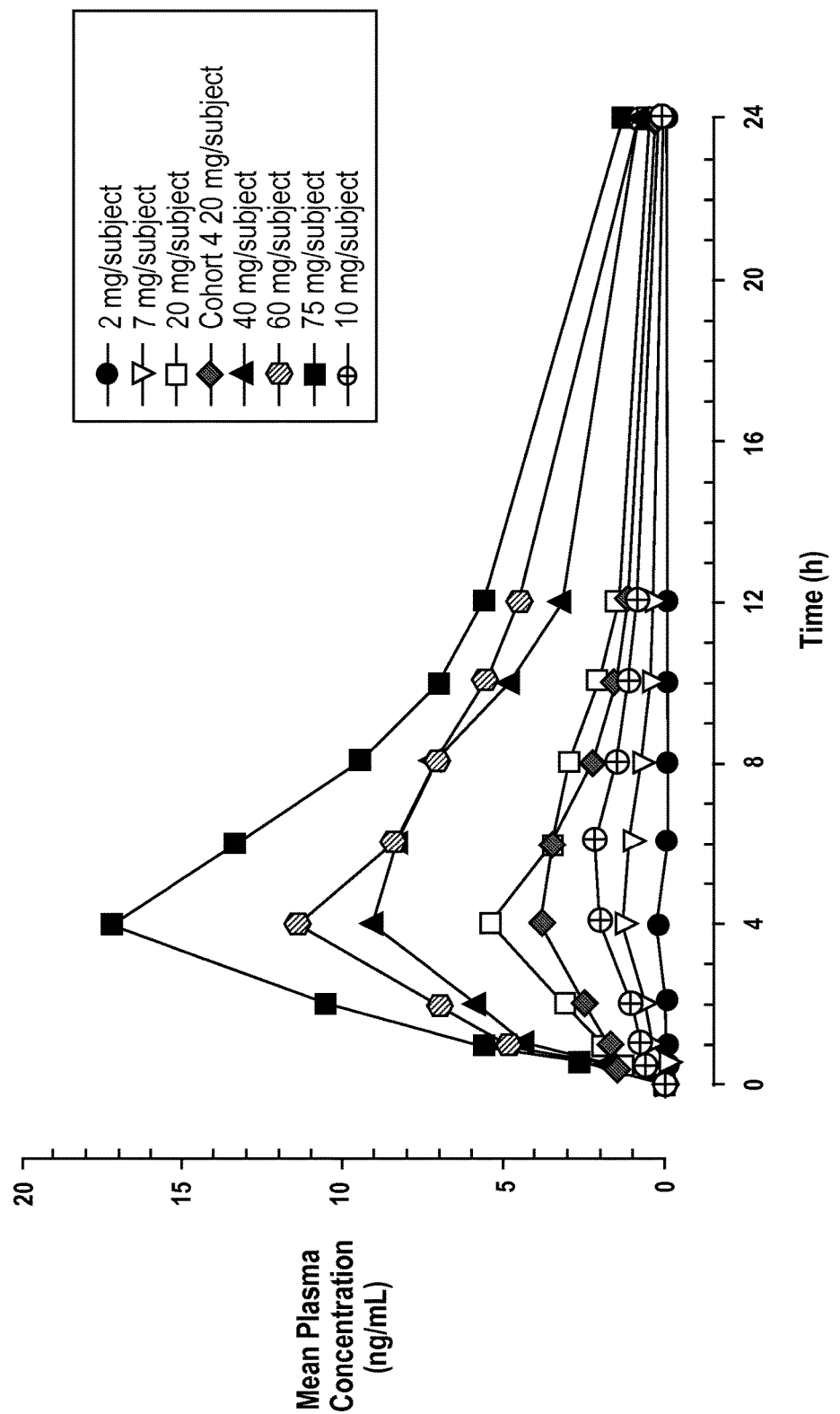
FIG. 9 provides the plasma concentration versus time graph as determined by the study described in Example 1.

A single-center, randomized, double masked, placebo controlled, dose-escalating Phase 1A study to determine the safety and pharmacodynamic effect of single dose oral (R)-3-amino-1-(3-(cyclohexylmethoxy)phenyl)propan-1-ol as measured by dark-adapted electroretinogram (ERG) was performed. Study participants were healthy volunteers of both genders, aged 55-80, weighing between 50 and 110 kg. Major exclusion criteria included other ocular conditions (e.g. cataracts, glaucoma, uveitis, diabetic retinopathy, active conjunctivitis), change in prescription chronic medications within the preceeding 28 days, treatment with a retinoid compound within the last year, treatment with sildenafil citrate, tadalafil, or vardenafil citrate within the last week, or concomitant treatment with hypnotics, anti-depressants, psychoactive substances, digitalis glycosides, L-DOPA, chloroquine, hydroxychloroquine, systemic corticosteroids, topical anti-glaucoma medications, or medications for the treatment of wet AMD. Eight cohorts were randomized 5:1/drug:placebo and assigned to dosage cohorts of 2 mg, 7 mg, 10 mg, 2×20 mg, 40 mg, 60 mg, and 75 mg. Plasma concentration versus time was determined and is shown in FIG. 9. Peak plasma concentrations ($C_{max}$) increased linearly with increasing dose. The test compound was readily absorbed from the GI tract and median time to attain $C_{max}$ was about 4 hours. Mean terminal elimination half-life ($t_{1/2}$) was 4-6 hours across all doses.

Figure 10:
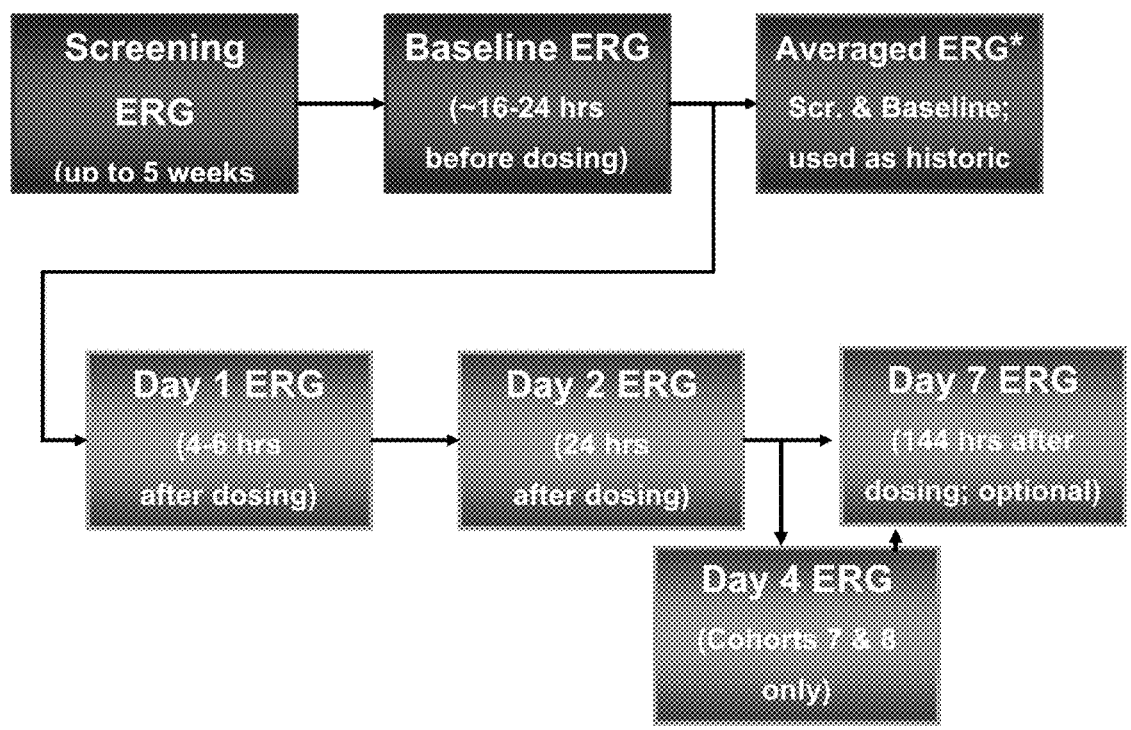
FIG. 10 provides the ERG data collection sequence utilized in the study described in Example 1.
Figure 11:
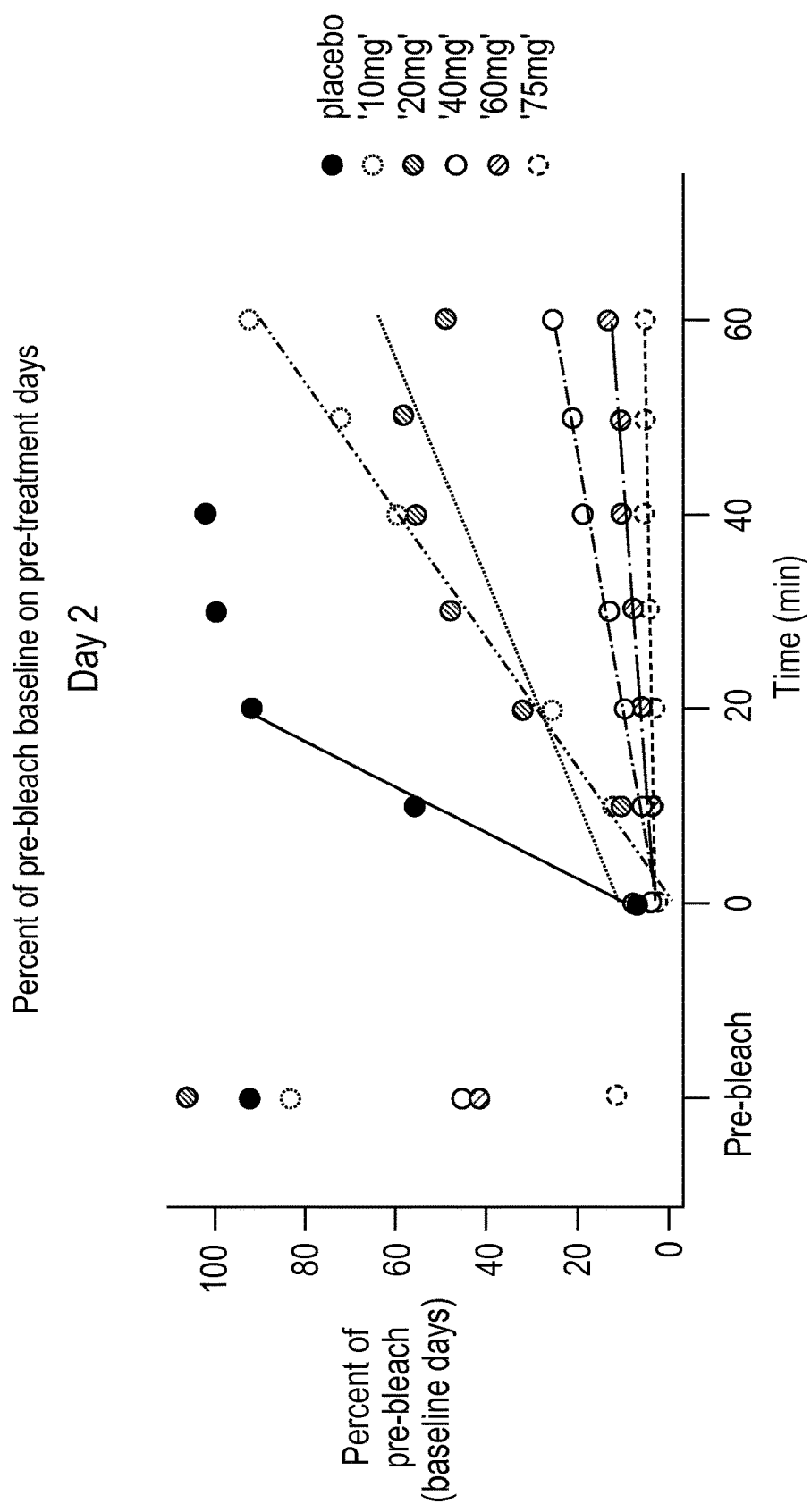
FIG. 11 provides the Day 2 ERG response curve obtained as described in Example 1.

ERG studies were performed prior to dosing, 4-6 hours post-dose (Day 1 ERG), 24 hours post-dose (Day 2 ERG), optionally on Day 4, and on Day 7 (144 hours post-dose) as outlined in FIG. 10. The Day 2 EGR response curve is provided in FIG. 11. For patients given placebo, there was a rapid rise in amplitude such that the response was 90% recovered by 20 minutes. For patients given (R)-3-amino-1-(3-(cyclohexylmethoxy)phenyl)propan-1-ol, there was a clear dose-related slowing of the rate of recovery; i.e. the slope of the recovery function became slower with increasing dose. At the highest dose, the amplitude was still less than 10% of the baseline response after 60 minutes. The pre-bleach amplitude is indistinguishable from the pre-treatment value for the placebo, 10 mg and 20 mg groups; i.e. 40 minutes of dark adaptation was sufficient to produce a comparable ERG to the pre-treatment dark-adapted value. For the 40 mg dose, the pre-bleach amplitude was less than 50% of the dark-adapted amplitude prior to treatment i.e. 40 minutes of dark-adaptation after normal room light exposure was not sufficient to produce the normal dark-adapted amplitude. Higher doses had progressively more affect on the pre-bleach amplitude; at 75 mg dose the amplitude was 11% baseline. A summary of the ERG data from cohorts 3-8 over Days 1-7 is provided in FIG. 12.

Figure 13:
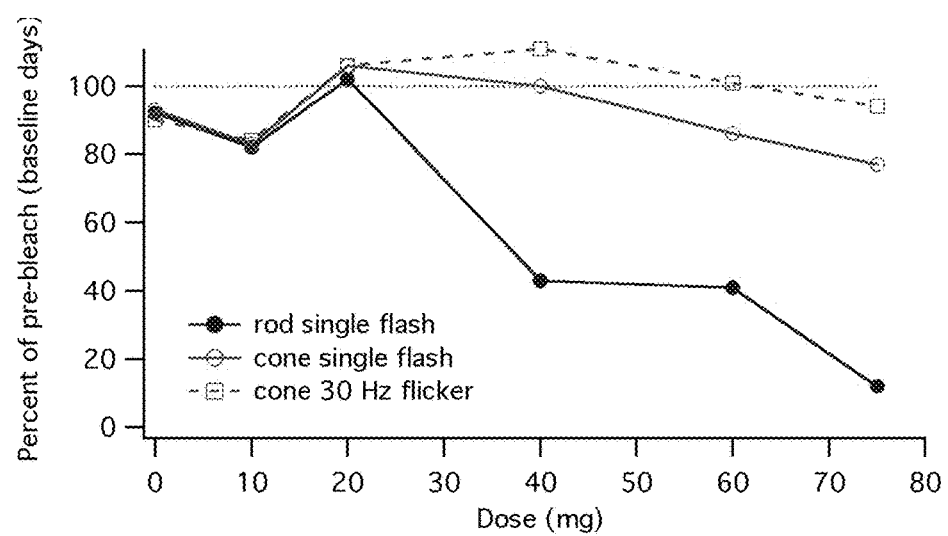
FIG. 13 provides the cone response curve as determined by the study described in Example 1.

A cone response curve determined on Day 2 is provided in FIG. 13. Unlike rod amplitudes, cone amplitudes remain within 20% of the pre-treatment amplitude for all doses. Doses of 40 mg and higher may cause noticeable deficiencies in night vision. There is no evidence that (R)-3-amino-1-(3-(cyclohexylmethoxy)phenyl)propan-1-ol will have a detectable effect on sensitivity in photopic (daylight) conditions.

Example 2—Treatment of Dry-Form Age Related Macular Degeneration

An individual diagnosed with dry-form age related macular degeneration is treated with an oral dose of 5 mg (R)-3-amino-1-(3-(cyclohexylmethoxy)phenyl)propan-1-ol every morning upon waking. On days 2, 4, 6, 8, 12, 18, 24 and 30 the individual is subjected to an electroretinogram determination to evaluate treatment response and the individual is monitored for instances of delayed dark adaptation and achromatopsia, as well as systemic adverse effects.

Example 3—Preparation of a Controlled Release Formulation

Nonpareil (granulated sucrose) having the diameter of 350 to 500 micrometers (80 g) is put into the centrifugal fluidizing type granulating and coating apparatus and to this is gradually added a fine powder of (R)-3-amino-1-(3-(cyclohexylmethoxy)phenyl)propan-1-ol (900 g) while spraying a solution of polyvinylpyrrolidone (20 g) dissolved in a mixture of water and ethanol (3:2) (640 g). The nonpareil is thus coated around its surface with (R)-3-amino-1-(3-(cyclohexylmethoxy)phenyl)propan-1-ol and is obtained as a plain granule. This plain granule is spray-coated with a solution containing 30 parts of Eudragit RS, 10 parts of calcium stearate and 3 parts of triethyl citrate to obtain a controlled release pharmaceutical formulation containing (R)-3-amino-1-(3-(cyclohexylmethoxy)phenyl)propan-1-ol.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 4—A Phase 1, Open-Label, Randomized, Two-Way Crossover, Food-Effect and Pharmacokinetic Pilot Study Following a Single 25 mg Oral Dose of (R)-3-amino-1-(3-(cyclohexylmethoxy) phenyl)propan-1-ol in Healthy Subjects Objectives:
The objectives of this study were:
1. to determine the effect of food on the pharmacokinetics (PK) of a single oral dose of (R)-3-amino-1-(3-(cyclohexylmethoxy)phenyl)propan-1-ol in normal healthy subjects; and 2. to further assess the safety of (R)-3-amino-1-(3-(cyclohexylmethoxy)phenyl)propan-1-ol in normal healthy subjects.

Study Design:

This was an open-label, randomized, 2-way crossover, food-effect and PK study conducted in 12 healthy male and female subjects under either fasted conditions (10-hour fast) or fed conditions (after standard Food and Drug Administration [FDA] high-fat breakfast).

Subjects Planned and Analyzed:

Twelve subjects were enrolled, completed the study, and were included in the analyses of safety and PK.

Diagnosis and Main Criteria for Inclusion:

Subjects were male or female; between 25 and 55 years of age (inclusive); with a body mass index (BMI) between 18.5 and 32.0 kg/m$^2$; a non-smoker; and in good health based upon results of medical history, physical examination, 12-lead electrocardiogram (ECG; within normal limits), laboratory test results, and visual status examinations.

Test Product, Dose, Route, Lot Number:

Subjects received a single oral dose of 25 mg (R)-3-amino-1-(3-(cyclohexylmethoxy)phenyl)propan-1-ol with 240 mL room temperature water after an approximately 10-hour fast and after a standard FDA high-fat breakfast in a crossover design according to a statistical randomization schedule.

Criteria for Evaluation:

Pharmacokinetic: For each subject, the following PK parameters were calculated, whenever possible, using non-compartmental methods:

$C_{max}$ Maximum observed plasma concentration.

$T_{max}$ Time to maximum plasma concentration.

$AUC_{0-t}$ Area under the plasma concentration-time curve from hour 0 to the last measurable plasma concentration, calculated by the linear up/log down trapezoidal rule.

$AUC_{0-\infty}$ Area under the plasma concentration-time curve extrapolated to infinity, calculated using the formula:

$$AUC_{0-\infty} = AUC_{0-t} + \frac{C_t}{\lambda_Z}$$

where $C_t$ is the last measurable plasma concentration and $\lambda_Z$ is the apparent terminal phase rate constant.

$\lambda_Z$ Apparent terminal phase rate constant, where $\lambda_Z$ is the magnitude of the slope of the linear regression of the log concentration versus time profile during the terminal phase.

$t_{1/2}$ Apparent terminal elimination half-life (whenever possible), where $t_{1/2} = (\ln 2)/\lambda_Z$.

CL/F Apparent oral clearance, calculated as Dose/$AUG_{0-\infty}$ in plasma.

Pharmacokinetic calculations were performed using the commercial software WinNonlin (Pharsight Corporation, Version 5.2). Pharmacokinetic analysis used actual times as recorded on the Case Report Form. For PK analysis, concentration values below the level of quantification (BLQs) at the beginning of the profile were set to 0; any embedded BLQs (between 2 quantifiable concentrations) or BLQs at the end of the profile were set to missing.

Safety: Safety procedures included adverse event (AE) assessments, 12-lead ECGs, vital signs, physical examinations, and laboratory assessments.

Statistical Methods:

General: Data listings are provided for PK and safety data. Summary statistics were provided for data, if applicable. Subject eligibility data collected only at Screening or Check-in were not summarized in tables. Data analysis was performed using Statistical Analysis Software (SAS®) Version 9.1.

Pharmacokinetic: Descriptive statistics (mean, standard deviation [SD], and coefficient of variation [CV]) were calculated for the PK parameters. All statistics are reported as unadjusted values. Individual $C_{max}$, $AUC_{0-t}$, and $AUG_{0-\infty}$ following administration of (R)-3-amino-1-(3-(cyclohexylmethoxy)phenyl)propan-1-ol under fasting or fed state are presented graphically.

Safety: Descriptive statistics were calculated on the safety data. No inferential statistical analyses were planned or conducted.

Pharmacokinetic Results:

Administration of (R)-3-amino-1-(3-(cyclohexylmethoxy)phenyl)propan-1-ol with a high fat meal in test Treatment B increased $C_{max}$, $AUC_{0-\infty}$, and $AUC_{0-t}$, on average, 9.0%, 12.0%, and 13.0%, respectively, compared to those in a fasted condition in the reference Treatment A based on unadjusted means.

Safety Results:

Overall, 47 AEs were reported by 12 subjects, with 26 AEs reported in Period 1 and 21 AEs reported in Period 2. Twenty-four AEs were reported following administration of (R)-3-amino-1-(3-(cyclohexylmethoxy)phenyl)propan-1-ol in the fasted state and 23 AEs were reported following administration of (R)-3-amino-1-(3-(cyclohexylmethoxy)phenyl)propan-1-ol in the fed state. The AE with the highest reported incidence overall was chromatopsia. All 12 subjects in this study reported at least 1 AE in the eye disorders system organ class, including chromatopsia, visual impairment, vision blurred, and tunnel vision.

All reported AEs were mild in severity. The relationship to study drug of the reported AEs was: 1 unrelated AE, 4 possibly related AEs, and 42 probably related AEs. There were no deaths or SAEs during this study and no AE led to study discontinuation. All AEs resolved without treatment by the end of the study.

No clinically significant changes or findings were noted from clinical laboratory evaluations, vital sign measurements, physical examinations, or 12-lead ECGs for this study. Overall, the changes in the clinical safety assessments were unremarkable.

Conclusions

Administration of (R)-3-amino-1-(3-(cyclohexylmethoxy)phenyl)propan-1-ol with food in test Treatment B increased $C_{max}$, $AUC_{0-\infty}$, and $AUC_{0-t}$, on average, 9.0%, 12.0%, and 13.0%, respectively, compared to without food in the reference Treatment A based on unadjusted means.

A single oral dose of 25 mg (R)-3-amino-1-(3-(cyclohexylmethoxy)phenyl)propan-1-ol was generally well-tolerated when given to healthy subjects in both the fed and fasted states.

What is claimed is:

1. A method of treating Stargardt's macular dystrophy, comprising administering daily a single oral dose of an amount from about 5 mg to about 10 mg of a non-retinoid compound (R)-3-amino-1-(3-(cyclohexylmethoxy)phenyl)propan-1-ol having the formula:

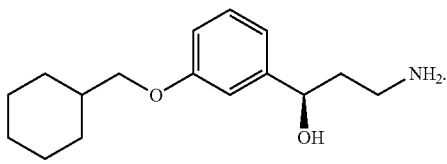 [SMILES: NCC[C@@H](O)c1cccc(OCC2CCCCC2)c1]

2. The method of claim 1, wherein the normalized electroretinogram response is from about 5% to about 15%, from about 15% to about 25%, from about 25% to about 35%, or from about 35% to about 50%.

3. The method of claim 1, wherein the normalized electroretinogram response is determined after about 12 hours to about 16 hours, after about 16 hours to about 20 hours, after about 20 hours to about 24 hours, after about 24 hours to about 30 hours, after about 30 hours to about 36 hours, after about 36 hours to about 42 hours, post administration of said non-retinoid compound.

4. The method of claim 1, wherein administration of a single dose of the non-retinoid compound results in a greater normalized electroretinogram response on day 1 than on day 2.

5. The method of claim 1, wherein administration of the non-retinoid compound results in a greater therapeutic response on day 2 than on day 1 after the administration of a single dose.

6. The method of claim 5, wherein the therapeutic response is determined by electroretinography.

7. The method of claim 1, wherein administration of the non-retinoid compound results in a normalized electroretinogram response of less than about 50% for a time period of about 4 hours to about 10 hours, about 10 hours to about 16 hours, about 16 hours to about 24 hours, or about 24 hours to about 36 hours after the plasma concentration of said non-retinoid compound has declined to 0.3 $C_{max}$.

8. The method of claim 1, wherein non-retinoid compound is administered in the morning, is administered upon waking from sleep, or is administered upon waking from sleep in the morning.

9. The method of claim 1, wherein the amount administered is about 5 mg, about 7 mg, or about 10 mg of the non-retinoid compound.

10. The method of claim 1, wherein the cone response amplitude of the electroretinogram remains within about 10%, within about 20%, or within about 30% of the pre-treatment amplitude.

11. The method of claim 1, wherein the dosage of non-retinoid compound is adjusted to provide no noticeable deficiency in night vision.

12. The method of claim 1, wherein the method results in no detectable effect on sensitivity in photopic conditions.

13. The method of claim 1, wherein the non-retinoid compound is an in the form of a controlled-release solid dosage form.

14. The method of claim 13, wherein administration of the controlled-release solid dosage form results in a plasma $T_{max}$ 12 hours post-administration.

15. The method of claim 1, wherein non-retinoid compound is administered at a time other than the morning.

16. The method of claim 15, wherein non-retinoid compound is administered during lunch or subsequent to lunch.

17. The method of claim 1, wherein the administration of the non-retinoid compound results in a normalized electroretinogram response of less than about 50% for a time period of about 4 hours to about 36 hours after the plasma concentration of the compound has declined to 0.3 $C_{max}$ following administration.

18. The method of claim 1, wherein the administration of the non-retinoid compound results in no noticeable loss in photopic vision.

19. The method of claim 1, wherein the administration of the non-retinoid compound results in no noticeable deficiency in night vision.

* * * * *